United States Patent
Gronthos et al.

(10) Patent No.: US 10,421,946 B2
(45) Date of Patent: *Sep. 24, 2019

(54) PERIVASCULAR MESENCHYMAL PRECURSOR CELLS

(71) Applicant: Mesoblast, Inc., New York, NY (US)

(72) Inventors: Stan Gronthos, Adelaide (AU);
Andrew Zannettino, Highbury (AU);
Songtao Shi, North Potomac, MD (US)

(73) Assignee: MESOBLAST, INC., New York, NY (US)

(*) Notice: Subject to any disclaimer, the term of this patent is extended or adjusted under 35 U.S.C. 154(b) by 347 days.

This patent is subject to a terminal disclaimer.

(21) Appl. No.: 14/746,960

(22) Filed: Jun. 23, 2015

(65) Prior Publication Data

US 2015/0368614 A1 Dec. 24, 2015
US 2017/0204373 A9 Jul. 20, 2017

Related U.S. Application Data

(63) Continuation of application No. 13/098,892, filed on May 2, 2011, now abandoned, which is a continuation of application No. 10/551,162, filed as application No. PCT/AU2004/000416 on Mar. 29, 2004, now Pat. No. 7,947,266.

(30) Foreign Application Priority Data

Mar. 28, 2003 (AU) ................................ 2003901668

(51) Int. Cl.
| | | |
|---|---|---|
| *C12N 5/0775* | (2010.01) | |
| *A61K 35/28* | (2015.01) | |
| *C12N 5/071* | (2010.01) | |
| *A61K 35/44* | (2015.01) | |
| *A61K 9/00* | (2006.01) | |
| *A61K 38/00* | (2006.01) | |

(52) U.S. Cl.
CPC .......... *C12N 5/0663* (2013.01); *A61K 9/0014* (2013.01); *A61K 35/28* (2013.01); *A61K 35/44* (2013.01); *C12N 5/0668* (2013.01); *C12N 5/0691* (2013.01); *A61K 38/00* (2013.01); *C12N 2500/42* (2013.01); *C12N 2501/11* (2013.01); *C12N 2501/135* (2013.01); *C12N 2501/165* (2013.01); *C12N 2501/235* (2013.01); *C12N 2501/39* (2013.01); *C12N 2506/1392* (2013.01)

(58) Field of Classification Search
None
See application file for complete search history.

(56) References Cited

U.S. PATENT DOCUMENTS

| | | |
|---|---|---|
| 5,197,985 A | 3/1993 | Caplan et al. |
| 5,226,914 A | 7/1993 | Caplan et al. |
| 5,405,722 A | 1/1995 | Ponting et al. |
| 5,486,359 A | 1/1996 | Caplan et al. |
| 5,580,754 A | 12/1996 | Samal |
| 5,591,625 A | 1/1997 | Gerson et al. |
| 5,811,094 A | 9/1998 | Caplan et al. |
| 5,827,740 A | 10/1998 | Pittenger |
| 5,837,539 A | 11/1998 | Caplan et al. |
| 5,922,597 A | 7/1999 | Verfaille et al. |
| 5,980,887 A | 11/1999 | Isner et al. |
| 6,022,540 A | 2/2000 | Bruder et al. |
| 6,087,113 A | 7/2000 | Caplan et al. |
| 6,261,549 B1 | 7/2001 | Fernandez et al. |
| 6,322,784 B1 | 11/2001 | Pittenger et al. |
| 6,335,195 B1 | 1/2002 | Rodgers et al. |
| 6,387,367 B1 | 5/2002 | Davis-Sproul et al. |
| 6,387,369 B1 | 5/2002 | Pittenger et al. |
| 6,645,727 B2 | 11/2003 | Thomas et al. |
| 6,709,864 B1 | 3/2004 | Pittinger et al. |
| 6,875,430 B2 | 4/2005 | McIntosh et al. |
| 7,122,178 B1 | 10/2006 | Simmons et al. |
| 2002/0085996 A1 | 7/2002 | McIntosh et al. |
| 2004/0107453 A1 | 6/2004 | Furcht et al. |
| 2005/0019911 A1 | 1/2005 | Gronthos et al. |
| 2005/0158289 A1 | 7/2005 | Simmons et al. |
| 2005/0281790 A1 | 12/2005 | Simmons et al. |

(Continued)

FOREIGN PATENT DOCUMENTS

| | | |
|---|---|---|
| WO | WO 99/003973 A | 1/1999 |
| WO | WO 00/06701 | 2/2000 |

(Continued)

OTHER PUBLICATIONS

International Search Report issued by the International Searching Authority (ISA/AU) dated May 17, 2004 in connection with International Application No. PCT/AU2004/000416.
International Publication No. WO 2001/004268 A1, Medvet Science Pty Ltd, published Jan. 18, 2001.
Shi S, Robey PG, and Gronthos S. (2001) Comparison of Human Dental Pulp and Bone Marrow Stromal Cells by cDNA Microarray Analysis. *Bone* 29(6): 532-539.

(Continued)

*Primary Examiner* — Michail A Belyavskyi
(74) *Attorney, Agent, or Firm* — John P. White; Gary J. Gershik; Cooper & Dunham LLP

(57) ABSTRACT

Mesenchymal precursors cells have been isolated from perivascular niches from a range of tissues utilizing a perivascular marker. A new mesenchymal precursor cell phenotype is described characterized by the presence of the perivascular marker 3G5, and preferably also alpha smooth muscle actin together with early developmental markers such as MUC 18, VCAM-1 and STRO-1$^{bri}$. The perivascular mesenchymal precursor cell is multipotential and is shown to form, vascular tissue, as well as bone marrow dentin and pulp. A method of enriching using cell sorting based on these markers is also described.

30 Claims, 19 Drawing Sheets

Specification includes a Sequence Listing.

(56) References Cited

U.S. PATENT DOCUMENTS

| | | |
|---|---|---|
| 2006/0008452 A1 | 1/2006 | Simmons et al. |
| 2006/0193840 A1 | 8/2006 | Gronthos et al. |
| 2006/0286007 A1 | 12/2006 | Galewski |
| 2006/0286077 A1 | 12/2006 | Gronthos et al. |
| 2007/0274958 A1 | 11/2007 | Shi et al. |
| 2008/0260694 A1 | 10/2008 | Gronthos et al. |
| 2009/0029912 A1 | 1/2009 | Gronthos et al. |

FOREIGN PATENT DOCUMENTS

| | | |
|---|---|---|
| WO | WO 01/011011 | 2/2001 |
| WO | WO 02/007679 A2 | 1/2002 |
| WO | WO 02/064748 A1 | 8/2002 |
| WO | WO 04/84921 A1 | 10/2004 |
| WO | WO 04/85630 A1 | 10/2004 |

OTHER PUBLICATIONS

Jones EA, Kinsey SE, English A, Jones RA, Straszynski L, Meredith DM, Markham AF, Jack A, Emery P, and McGonagle D. (2002) Isolation and Characterization of Bone Marrow Multipotential Mesenchymal Progenitor Cells. *Arthritis Rheum.* 46(12): 3349-3360.
Gronthos S, Brahim J, Li W. Fisher LW, Cherman N, Boyde A, DenBesten P, Gehron Robey P. and Shi S. (2002) Stem Cell Properties of Human Dental Pulp Stem Cells. *J. Dent. Res.* 81(8):531-535.
International Preliminary Report on Patentability issued by the International Bureau of WIPO dated Oct. 1, 2005 in connection with International Application No. PCT/AU2004/000416.
Shi S et al: "Perivascular niche of postnatal mesenchymal stem cells in human bone marrow and dental pulp." Journal of Bone and Mineral Research, vol. 17, No. Suppl 1, Sep. 2002 (Sep. 2002), p. S446, XP009083412 & Twenty-Fourth Annual meeting of the American Society for Bone Mineral Research; San Antonio, Texas, USA; Sep. 20-24, 2002.
Jones Elena A et al: "Isolation and characterization of bone marrow multipotential mesenchymal progenitor cells." Arthritis and Rheumatism Dec. 2002, vol. 46, No. 12, Dec. 2002 (Dec. 2002).
Gronthos S et al: "Postnatal human dental pulp stem cells (DPSCs) in vitro and in vivo. "Proceedings of the National Academy of Sciences of USA, National Academy of Science, Washington, DC, US, vol. 97, No. 25, Dec. 5, 2000 (Dec. 5, 2000), pp. 13625-13630.
Shi S et al: "Comparison of human dental pulp and bone marrow stromal stem cells by cDNA microarray analysis." Bone, Pergamon Press., Oxford, GB, vol. 29, No. 6, Dec. 2001 (Dec. 2001).
Shi S et al: "Perivascular niche of postnatal mesenchymal stem cells in human bone marrow and dental pulp." Journal of Bone and Mineral Research, New York, NY, US, vol. 18, No. 4, Apr. 2003 (Apr. 2003), pp. 696-704.
Gronthos Stan et al: "Molecular and cellular characterization of highly purified stromal stem cells derived from human bone marrow." Journal of Cell Science, vol. 116, No. 9, May 1, 2003 (May 1, 2003), pp. 1827-1835.
Tse H F et al: "Angiogenesis in ischaemic myocardium by intramyocardial autologous bane marrow mononuclear cell implantation." Lancet The, Lancet Limited, London, GB, vol. 361, No. 9351, Jan. 4, 2003 (Jan. 4, 2003), pp. 47-49.
Supplementary European Search Report from European Patent Office, Application No. EP 04 72 3935, dated May 10, 2007.
Supplementary European Search Report from European Patent Office, Application No. EP 04 72 3937, dated May 25, 2007.
Hellström M, Kalén M, Lindahl P, Abramsson A, and Betsholtz C. (1999) Role of PDGF-B and PDGFR-β in recruitment of vascular smooth muscle cells and pericytes during embryonic blood vessel formation in the mouse. Development 126: 3047-3055.
International Search Report issued by the International Searching Authority (ISA/AU) dated May 17, 2004 in connection with International Application No. PCT/AU2004/000417.

International Preliminary Report on Patentability issued by the International Bureau of WIPO dated Oct. 1, 2005 in connection with International Application No. PCT/AU2004/000417.
Alberico et al. (1987) Blood 69, pp. 1120-1127.
Allen, T.D., (1981) "Haemopoietic Microenvironments in vitro:ultrastructural aspects" CIBA Found. Symposium 84, pp. 38-67.
Allen et al. (1990) "Marrow Biology and Stem Cells" Immunol. Ser. 49, pp. 1-38.
Anklesaria et al. (1989) Blood 74, pp. 1144-1151.
Anklesaria et al. (1987) Proc. Nat'l Acad. Sci. USA 84, pp. 7681-7685.
Bennett, J.H. et al. (1991) J. Cell Sci. 99, pp. 131-139.
Bentley, S.A. (1982) Br. J. Haematol 50(1), pp. 1-6.
Castro-Malaspina et al. (1980) "Characterization of Human Bone Marrow Fibroblast Colony-Forming Cells and Their Progeny" Blood 56, pp. 289-301.
Castro-Malaspina et al. (1981) "Human Megakaryocyte Stimulation of Proliferation of Bone Marrow Fibroblasts" Blood 57, pp. 781-787.
Clarke, Emer, "Mesenchymal Cells" www.stemcell.com (mini-review).
Dexter et al. (1977) "Conditions Controlling the Proliferation of Haemopoietic Stem Cells in Vitro" J. Cell Physiol. 91, pp. 335-344.
Dexter et al. (1984) Kroc Found. Ser. 18, pp. 57-96.
Doherty, M.J. et al. (1998) "Vascular Pericytes Express Osteogenic Potential In Vitro and In Vitro" J. Bone and Mineral Research 13, pp. 828-838.
Fong et al. (1997) "Nonradioactive, Agarose Minigel Procedure for Telomeric Repeat Amplification Protocol" BioTechniques 23, pp. 1029-1032.
Friedenstein (1976) Int'l R. Cytology 47, pp. 327-359.
Friedenstein (1980) "Stromal Mechanisms of Bone Marrow: Cloning in Vitro and Retransplantation in Vivo" Immunology of Bone Marrow Transplantation, pp. 19-29 Haematol. Blood Transfusion.
Friedenstein et al. (1970) "The Development of Fibroblast Colonies in Monolayer Cultures of Guinea-Pig Bone Marrow and Spleen Cells" Cell Tissue Kinetics 3, pp. 393-403.
Friedenstein et al. (1992) Bone and Mineral 18, pp. 199-213.
Gronthos, S., et al. (1994) "The STRO-1+ Fraction of Adult Human Bone Marrow Contains the Osteogenic Precursors," Blood 84, pp. 4164-4173.
Gronthos, S., et al. (1995) Blood 85, pp. 929-940.
Huang and Terstappen (1992) Nature 360, pp. 745-749.
Keating et al. (1982) Nature 298, pp. 280-283.
Kim et al. (1994) Science 266, pp. 2011-2015.
Knospe et al. (1966) Blood 28, pp. 398-415.
Knospe et al. (1972) Blood 39, pp. 331-340.
Lichtman (1981) Experimental Hematology 9, pp. 391-410.
Long (1992) Experimental Hematology 20, pp. 288-301.
McManus and Weiss (1984) Blood 64, pp. 1036-1041.
McIntyre and Bjornson (1986) Exp. Hematol. 14, pp. 833-839.
Miltenyi et al. (1990) Cytometry 11, pp. 231-238.
Owen (1985) Bone and Mineral Research 3, pp. 1-25.
Owen and Friedenstein (1988) CIBA Found. Symposium 136, pp. 42-60.
Perkins and Fleischman (1990) Blood 75, pp. 620-625.
Piersma et al. (1983) Br. J. Haematol. 54, pp. 285-290.
Rothstein et al. (1985) Blood 65, p. 744.
Simmons and Gronthos (1991) Int'l J. Cell Cloning 9, p. 408 (abstract).
Simmons, P.J., et al. (1994) "Isolation, Characterization and Functional Activity of Human Marrow Stromal Progenitors in Hemopoiesis" Advances in Bone Marrow Purging and Processing: Progress in Clinical and Biological Research; Fourth Int'l Symposium 389, pp. 271-280.
Simmons et al. (1987) Nature 328, pp. 429-432.
Simmons and Torok-Storb (1991) Blood 78, pp. 55-62.
Simmons and Torok-Storb (1991) Blood 78, pp. 2848-2853.
Tavassoli and Friedenstein (1983) Ann. J. Hematol. 15, pp. 195-203.
Testa et al. (1988) "Long-Term Bone Marrow Damage After Cytotoxic Treatment: Treatment: Stem Cells and Microenvironment in

(56) References Cited

OTHER PUBLICATIONS

Hematopoiesis: Long-Term Effects of Chemotherapy and Radiation" Hematol. Published by Marcel & Deaker, Inc. 8, pp. 75-91.
Van Vlasselaer et al. (1994) Blood 84, pp. 753-763.
Waller et al. (1995) Blood 85, pp. 2422-2435.
Weiss (1976) Anatomical Record 186, pp. 161-184.
Zóltowska A, Stepiński J, Lewko B, Zamorska B, Roszkiewicz A, Serkies K, and Kruszewski WJ. (2001) Malformations of Angiogenesis in the Low Differentiated Human Carcinomas. Immunohistochemical Study. Arch. Immunol. Ther. Ex. 49: 59-61.
Axelrad et al., New Technologies for the Enhancement of Skeletal Repair, Injury, Int. J. Care Injured (2007) 38S1:S49-S62.
Bruder et al., Mesenchymal Stem Cells in Bone Development, Bone Repair, and Skeletal Regeneration Therapy, J. Cell Biochem; (1994) 56:283-294.
Dennis et al., Osteogenesis in Marrow-Derived Mesenchymal Cell Porous Ceramic Composites Transplanted Subcutaneously: Effect of Fibronectin and Laminin on Cell Retention and Rate of Osteogenic Expression, Cell Transplant (1992) 1:23-32, Abstract.
Zvaifler, et al., (2000) "Mesenchymal precursor cells in the blood of normal individuals," Arthritis Research and Therapy, 2: 477-488.
Ji, et al., (2004) "Interactions of Chemokines and Chemokine Receptors Mediate the Migration of Mesenchymal Stem Cells to the Impaired Site in the Brain After Hypoglossal Nerve Injury," Stem Cells, 22: 415-427.
Sordi, et al., (2005) "Bone marrow mesenchymal stem cells express restricted set of functionally active chemokine receptors capable of promoting migration to pancreatic islets," Blood, 106(2): 419-427.
Wynn, et al., (2004) "A small proportion of mesenchymal stem cells strongly expresses functionally active CXCR4 receptor capable of promoting migration to bone marrow," Blood, 104(9): 2643-2645.
Kortesidis, et al., (2005) "Stromal-derived factor-1 promotes the growth, survival, and development of human bone marrow stromal stem cells," Blood, 105(10): 3793-3801.
Gronthos, S., et al., (1999) "Differential Cell Surface Expression Of The STRO-1 And Alkaline Phosphatase Antigens On Discrete Developmental Stages In Primary Culture Of Human Bone Cells," Journal of Bone and Mineral Research, 14(1): 47-56.
Stewart, K., et al., (1999) "Further Characterization Of Cells Expressing STRO-1 In Cultures Of Adult Human Bone Marrow Stromal Cells," Journal of Bone and Mineral Research, 14(8): 1345-1356.
International Search Report issued by the International Searching Authority (ISA/AU) dated Aug. 22, 2005 in connection with International Application No. PCT/AU2005/000953.
International Search Report issued by the International Searching Authority (ISA/AU) dated Nov. 25, 2005 in connection with International Application No. PCT/AU2005/001445.
Office Action dated Jan. 12, 2005 in connection with U.S. Appl. No. 10/030,411.
Office Action dated Jun. 28, 2005 in connection with U.S. Appl. No. 10/030,411.
Final Office Action dated Jan. 9, 2006 in connection with U.S. Appl. No. 10/030,411.
Office Action dated Apr. 20, 2007 in connection with U.S. Appl. No. 10/955,709.
Office Action dated Aug. 24, 2007 in connection with U.S. Appl. No. 11/178,920.
Office Action dated Aug. 25, 2006 in connection with U.S. Appl. No. 110/955,709.
Examiner Interview Summary dated Jun. 27, 2006 in connection with U.S. Appl. No. 10/030,411.
Office Action dated Dec. 15, 2006 in connection with U.S. Appl. No. 11/178,920.
Office Action dated Jul. 10, 2006 in connection with U.S. Appl. No. 11/178,920.
Office Action dated Jan. 22, 2007 in connection with U.S. Appl. No. 11/169,875.
Office Action dated Jul. 10, 2006 in connection with U.S. Appl. No. 10/813,747.
Office Action dated Dec. 15, 2006 in connection with U.S. Appl. No. 10/813,747.
Office Action dated Apr. 3, 2007 in connection with U.S. Appl. No. 10/813,747.
Office Action dated Oct. 19, 2007 in connection with U.S. Appl. No. 10/813,747.
Restriction Requirement dated Jan. 8, 2008 in connection with U.S. Appl. No. 11/326,736.
Final Office Action dated Jan. 10, 2008 in connection with U.S. Appl. No. 10/955,709.
Extended European Search Report dated Dec. 27, 2007 in connection with European Application No. 05787106.3.
Supplementary European Search Report dated Jan. 2, 2008 in connection with European Application No. 05754008.0.
Cochlovius, B. et al. (2003) "Therapeutic Antibodies," Modern Drug Discovery pp. 33-34, 37-38.
Gronthos et al. Journal of Hematotherapy, 1996. 5, 15-23 (Abstract).
Hansson, M. et al. (2007) "Commentary: Isolated Stem Cells—Patentable as Cultural Artifacts?" V.25, pp. 1507-1510.
Pan, Beiqing et al. (2004) "The nitrogen-containing bisphosphonate, zaledronic acid, increases mineralisation of human bone-derived cells in vitro." Bone 34:112-123.
Cassiede, P. et al. (1996) "Osteochondrogenic Potential of Marrow Mesenchymal Progenitor Cells Exposed to TGF- β1 or PDGF-BB as Assayed In Vivo and In Vitro" Journal of Bone and Mineral Research vol. 11(9):1264-1273.
Kang Yong Jung et al. (2004) "Involvement of PI-3-kinase, JNK, PKC, and PKA in the PDGF-induced proliferation in himan adipose tissue-derived mesenchymal stem cells" vol. 18(8) p. C253.
Barry, F.P. (2003), "Biology and Clinical Applications of Mesenchymal Stem Cells," Birth Defect Research (Part C) 69:250-256.
Chopp, M. and Li, Y. (2002), "Treatment of Neural Injury with Marrow Stromal Cells," The Lancet Neurology 1:92-100.
Dennis JE, et al. (2002), "The STRO-1+ Marrow Cell Population is Multipotential," Cells Tissues Organs, 170:73-82.
Greenberger, J. and Keating, A. (1996), "The Hematopoietic Effects Microenvironment," Keystone Symposium, Taos, New Mexico 14:366-367.
Hoerstrup SP et al. (2002), "Tissue Engineering of Functional Trileaflet Heart Valves From Human Marrow Stromal Cells," Circulation 106(Suppl):I-1463-I-150.
Kassem, M. (2004), "Mesenchymal Stem Cells: Biological Characteristics and Potential Clinical Applications," Cloning Stem Cells 6:369-374.
Le Blanc, K. and Ringden, O. (2005), "Immunobiology of Human Mesenchymal Stem Cells and Future Use in Hematopoietic Stem Cell Transportation," Biology of Blood and Marrow Transplantation 11:321-334.
Murray et al. (1996), "Fetal Bone Marrow CD34 'CD41' Cells are Enriched for Multipotent Hematopoietic Progenitors, but not for Pluripotent Stem Cells," Exp. Hematol 24:236-245.
Summer, R. and Fine, A. (2008), "Mesenchymal Progenitor Limitations and Recommendations," Proc.Am, Thorac. Soc. 5:707-710.
Restriction Requirement dated Nov. 13, 2007 in connection with U.S. Appl. No. 11/169,875.
Office Action dated Oct. 16, 2008 in connection with U.S. Appl. No. 10/955,709.
Office Action dated Nov. 13, 2008 in connection with U.S. Appl. No. 10/551,326.
Office Action dated Nov. 17, 2008 in connection with U.S. Appl. No. 11/326,736.
Office Action dated Nov. 26, 2008 in connection with U.S. Appl. No. 11/169,875.
Finney, M.R. et al. (2006), "Direct Comparison of Umbilical Cord Blood versus Bone Marrow-Derived Endothelial Precursor Cells in mediating Neovascularization In Response to Vascular Ischemia," Biol. Blood and Marrow Transplant 12:585-59.
Yang XB, et al. (2006), "Evaluation of Human Bone Marrow Stromal Cell Growth on Biodegradable Polymer/Bioglass Composites," Biochem Biophys Res Commun 342:1098-1107.
Fuji, S. et al. (2008), "Investigating a Clonal Human Periodontal Ligament Progenitor/Stem Cell Line In Vitro and In Vivo," J. Cell Physiol. 215:743-749.

(56) References Cited

OTHER PUBLICATIONS

Bianco, P. et al. (2001), "Bone Marrow Stromal Stem Cells: Nature, Biology, and Potential Applications," Stem Cells 19:180-192.
Final Office Action dated Jun. 23, 2009 in connection with U.S. Appl. No. 11/169,875.
Final Office Action dated Jul. 16, 2009 in connection with U.S. Appl. No. 10/955,709.
Final Office Action dated Sep. 29, 2009 in connection with U.S. Appl. No. 10/551,326.
Final Office Action dated Oct. 8, 2009 in connection with U.S. Appl. No. 11/326,736.
Notice of Allowance dated Oct. 29, 2009 in connection with U.S. Appl. No. 10/813,747.
Final Office Action dated Dec. 9, 2009 in connection with U.S. Appl. No. 11/169,875.
Examination report dated Oct. 10, 2009 in connection with European Application No. 05754008.0.
Neuhaus T. et al. (2003), "Stromal cell-derived factor lalpha (SDF-lalpha) induces gene-expression of early growth response-1 (Egr-1) . . . " Cell Proliferation 36:75-86.
Salcedo R. et al. (1999), "Vascular endothelial growth factor and basic fibroblast growth factor induce expression of CXCR4 . . . " American Journal of Pathology 154:1125-1135.
Office Action dated Jan. 19, 2010 in connection with corresponding Japanese Application No. 2006-503989.
Office Action dated Mar. 16, 2010 in connection with U.S. Appl. No. 11/663,570.
Karibe K. et al. (2002), "Stimulation of Matrix Metalloprotease 3 Release from Human Chondrocytes by the Interaction of Stromal Cell . . . " Arthritis & Rheumatism 46:130-137.
Final Office Action dated Jun. 2, 2010 in connection with U.S. Appl. No. 11/169,875.
Office Action dated Sep. 22, 2009 in connection with U.S. Appl. No. 11/663,570.
Office Action dated Nov. 8, 2010 in connection with U.S. Appl. No. 12/660,003.
English language translation of Abstract of Japanese Patent Application Publication No. 2003-52365, published Feb. 25, 2003.
Helmbold P. et al. (2001) "Human dermal pericytes express 3G5 ganglioside—a new approach for microvessel histology in the skin" J Cutan Pathol. (4):206-10.
Restriction Requirement dated Jan. 8, 2008 in connection with U.S. Appl. No. 10/551,162, filed Sep. 28, 2005.
Office Action dated Sep. 12, 2008 in connection with U.S. Appl. No. 10/551,162, filed Sep. 28, 2005.
Final Office Action dated Jun. 22, 2009 in connection with U.S. Appl. No. 10/551,162, filed Sep. 28, 2005.
Office Action dated Aug. 26, 2010 in connection with U.S. Appl. No. 10/551,162, filed Sep. 28, 2005.
Notice of Allowance dated Jan. 14, 2011 in connection with U.S. Appl. No. 10/551,162, filed Sep. 28, 2005.
Opposition to Grant of Patent, filed Feb. 14, 2018, in connection with Japanese Patent No. 6188435.
Gronthos et al. (2001) "Surface Protein Characterization of Human Adipose Tissue-Derived Stromal Cells", Journal of Cellular Physiology 189:54-63.
Zuk et al. (2002) "Human Adipose Tissue is a Source of Multipotent Stem Cells", Molecular Biology of the Cell 13:4279-95.

US 10,421,946 B2

PERIVASCULAR MESENCHYMAL PRECURSOR CELLS

This application is a continuation of U.S. Ser. No. 13/098,892, filed May 2, 2011, which is a continuation of U.S. Ser. No. 10/551,162, filed Sep. 28, 2005, § 371 National Stage of PCT International Application No. PCT/AU2004/000416, filed Mar. 29, 2004, claiming priority of Australian Provisional Application No. 2003901668, filed Mar. 28, 2003, the contents of all of which are hereby incorporated by reference.

FIELD OF THE INVENTION

This invention relates to mesenchymal precursor cells, and the isolation of a subpopulation of such precursors carrying a perivascular marker.

BACKGROUND OF THE INVENTION

Numerous attempts at isolating and enriching mesenchymal precursor cells have been attempted because of the potential that these cells have for medicinal use. Pittinger et al., (1999) show the expansion of clonogenic cells from bone marrow and describes a preparation of enlarged mesenchymal stem cells. A more recent example of such a method providing for a relatively high yield from bone marrow is disclosed in publication WO01/04268 to Simmons et al.

To date however there have been no examples of methods that permit the isolation of mesenchymal precursor cells from a wide range of tissues.

SUMMARY OF THE INVENTION

The present invention arises from the finding that a population of multipotential mesenchmal precursor cells (MPCs) is present in a perivascular niche. This has led to the demonstration that there is a much wider range of tissue type sources of MPCs than the single tissue, bone marrow, referred to in WO01/04268. The present invention arises from the additional finding that an enriched population MPCs can be differentiated into two populations discriminated by the marker 3G5. MPCs that are 3G5 positive are considered of interest particularly for neovascularization applications, although demonstrably they are also shown to differentiate into other tissue types. It is an additional finding of the present invention that levels of MPCs present in preferred enriched populations of this invention are able to give rise to sufficient numbers of committed cells to provide a number of differentiated tissue types.

In a first form of a first aspect the invention might be said to reside in a method of enriching for mesenchymal precursor cells (MPCs), the method including the step of preparing a single cell suspension from a vascularised source tissue and the step of enriching based on the presence of an early perivascular cell marker.

In a second form of the first aspect the invention might be said to reside in a method of enriching for mesenchymal precursor cells (MPCs), the method including the step of preparing a single cell suspension from a, non-bone marrow, vascularised source tissue and separating the tissue into separate cells and the step of enriching based one of the presence or level of one or more early developmental markers and the absence of one or more surface markers indicative of commitment.

In a third form of the first aspect the invention might be said to reside in a method of enriching for mesenchymal precursor cells (MPCs), the method including the step of preparing a single cell suspension from a vascularised source tissue and the step of enriching based on the presence of markers expressed in the vascularized tissue by perivascular cells.

In a second aspect the invention might be said to reside in an enriched population of cells enriched for mesenchymal precursor cells (MPCs) said MPCs having a phenotype of 3G5, MUC18, VCAM-1, STRO-1$^{bri}$ and α smooth muscle actin.

In a first form of a third aspect the invention might be said to reside in an isolated mesenchymal precursor cells (MPCs) said MPCs having a phenotype of 3G5, MUC18, VCAM-1, STRO-1$^{bri}$ and α smooth muscle actin.

In a second form of the third aspect the invention might be said to reside in an isolated mammalian cell that is multipotent and that is positive for the surface marker 3G5.

In a third form of the third aspect the invention might be said to reside in a mesenchymal precursor cell (MPC), capable of forming a clonogenic colony and differentiating to three or more mesenchymal tissue types, isolated from a tissue of the group comprising, but not limited to, adipose tissue, teeth, dental pulp, skin, liver, kidney, heart, retina, brain, hair follicles, intestine, lung, spleen, lymph node, thymus, pancreas, bone, ligament, bone marrow, tendon, and skeletal muscle, and which is positive for the surface marker STRO-1.

In a fourth form of the third aspect the invention might be said to reside in an unexpanded population of cells enriched for mesenchymal precursor cells (MPCs), capable of forming a clonogenic colony and differentiating to three or more mesenchymal tissue types, said MPCs co-expressing the surface markers MUC18/CD146 and alpha-smooth muscle actin.

In a fourth aspect the invention might be said to reside in a differentated progeny cell arising from the third aspect of the invention preferably wherein the progeny cell is at least an osteoblast, odontoblast, dentin-producing, chondrocyte, tendon, ligament, cartilage, adipocyte, fibroblast, marrow stroma, osteoclast- and hematopoietic-supportive stroma, cardiac muscle, smooth muscle, skeletal muscle, pericyte, vascular, epithelial, glial, neuronal, astrocyte or oligodendrocyte cell.

sections near the bone (b) surface 20×. Sections were counter stained with Hematoxylin. (H) Dual Immunofluorescence staining demonstrating reactivity of the STRO-1 antibody labeled with Texas red and the CC9 antibody labeled with fluorescein isothiocyanate, reacting to blood vessel walls in frozen sections of human bone marrow.

Figure 2:
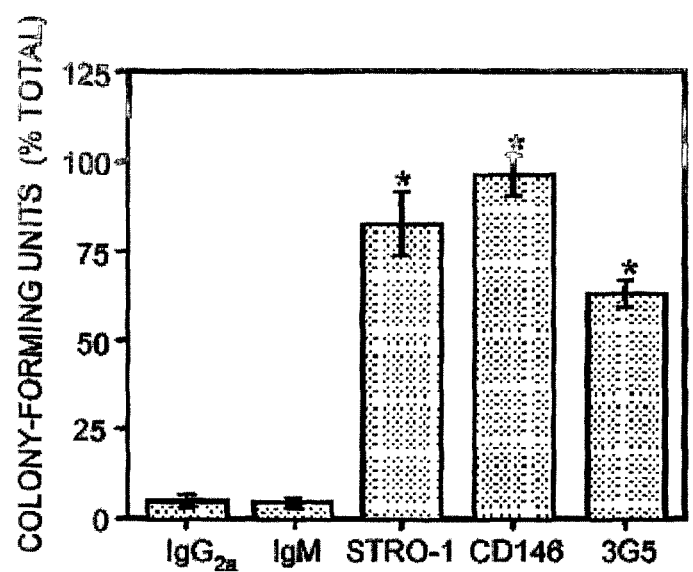

FIG. 2. Immunophenotypic analysis of DPSCs in vivo. The bar graph depicts the number of clonogenic colonies retrieved from single cell suspensions of dental pulp following immunomagnetic bead selection based on reactivity to antibodies that recognize STRO-1, CD146, and 3G5 and isotype-matched negative control antibodies. The data are expressed as the number of colony-forming units obtained in the bead positive cell fractions as a percentage of the total number of colonies in unfractionated pulp cells averaged from three separate experiments. Statistical significance (*) was determined using the student t-test (p 0.01) comparing the percent total number of colonies for each antibody with the corresponding isotype-matched control.

Figure 3:
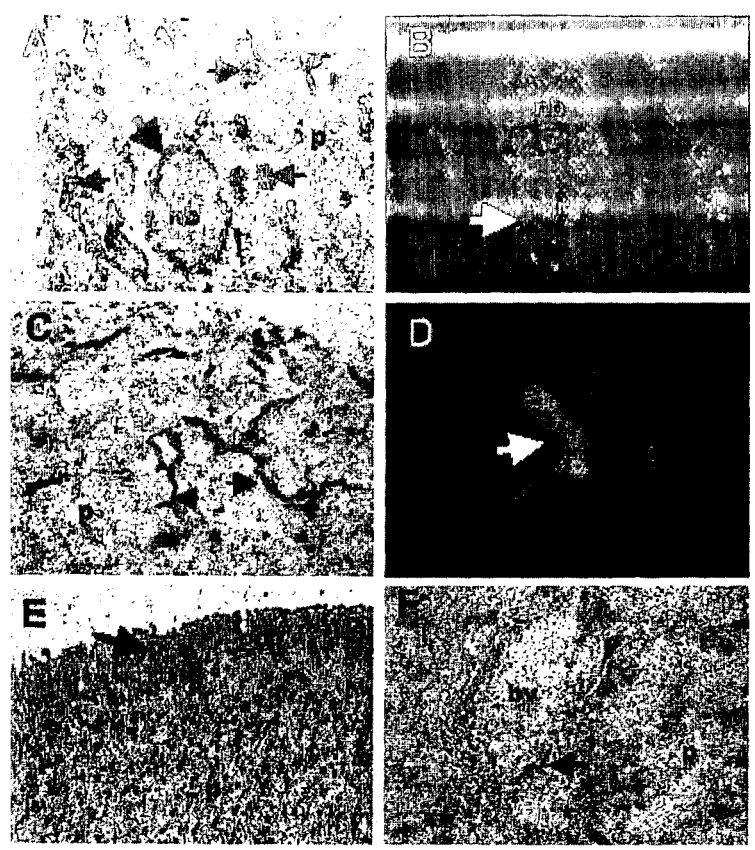

FIG. 3. Reactivity of perivascular makers in dental pulp. (A) Immunolocalization of the STRO-1 antigen on blood vessels (small arrows) in human dental pulp (p) and around perineurium (large arrow) surrounding a nerve bundle (nb) 20×. (B) Dual Immunofluorescence staining demonstrating reactivity of the STRO-1 antibody labeled with Texas Red to dental pulp perineurium (arrow) in combination with an anti-neurofilament antibody labeled with fluorescein isothiosyanate staining the inner nerve bundle (nb), 40×. (C) Immunolocalization of the CD146 antigen to blood vessel walls in human dental pulp tissue 20×. (D) Dual Immunofluorescence staining demonstrating reactivity of the STRO-1 antibody labeled with Texas red to a blood vessel and the CC9 antibody labeled with fluorescein isothiosyanate. (E) Immunohistochemical staining of pulp tissue with a rabbit polyclonal anti-DSP antibody (arrow) to the odontoblast outer layer (od). 20×. (F) 3G5 reactivity to a single pericyte (arrow) in a blood vessel (bv) wall 40×. Tissue sections were counter stained with Hematoxylin.

Figure 4:
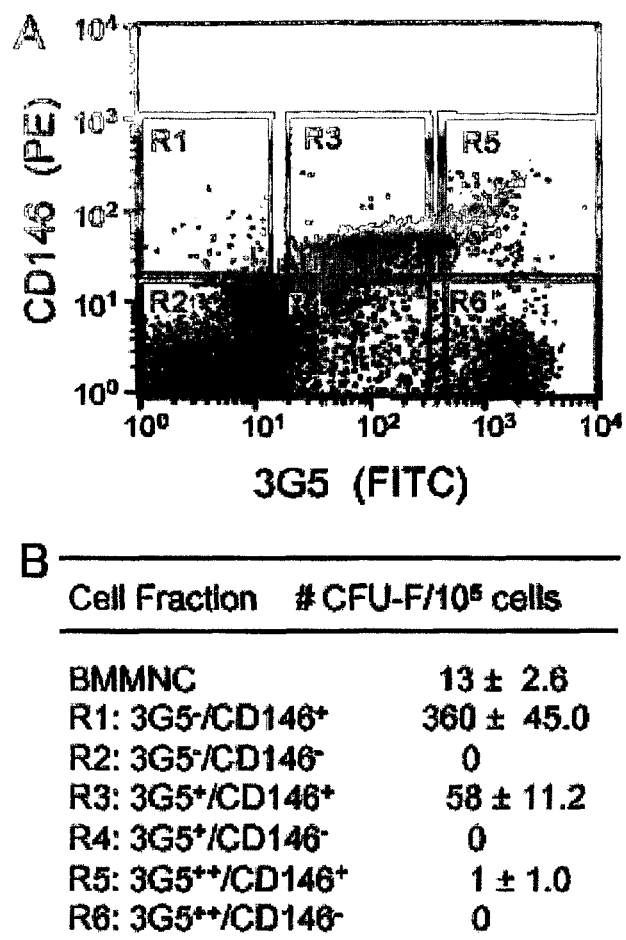

FIG. 4. 3G5 reactivity to BMSSCs. (A) The representative histogram depicts a typical dual-color FACS analysis profile of whole bone marrow mononuclear cells (BMMNCs) expressing CD146 (PE) and 3G5 (FITC). (B) Colony efficiency assays were performed for all the different expression patterns observed (regions "R" 1-6). The data are expressed as the mean incidence of colony-forming units for each cell fraction averaged from three separate experiments.

Figure 5:

FIG. 5. Developmental potential of purified BMSSCs and DPSCs in vivo. Cytospin preparations of MACS/FACS isolated STRO-1$^{BRT}$/CD146$^+$ marrow cells (arrow) stained with an antibody specific to α-smooth muscle actin (A) and von Willebrand Factor (B). CD146$^+$ pulp cells (large arrow) isolated by immunomagnetic bead selection (magnetic beads depicted by small arrows), stained with an antibody specific to α-smooth muscle actin (C) and von Willebrand Factor. (D). (E) Ectopic bone formation (b) and haematopoietic/adipogenic marrow (bm) by ex vivo expanded cells derived from STRO-1$^{BRT}$/CD146$^+$ BMSSCs transplanted with HA/TCP into immunocompromised mice for three months (E). (F) Ectopic formation of dentin (d) and fibrous pulp tissue (p) by ex vivo expanded cells derived from CD146$^+$ DPSCs transplanted with HA/TCP into immunocompromised mice for three months. Sections were stained with Hematoxylin & Eosin.

Figure 6:
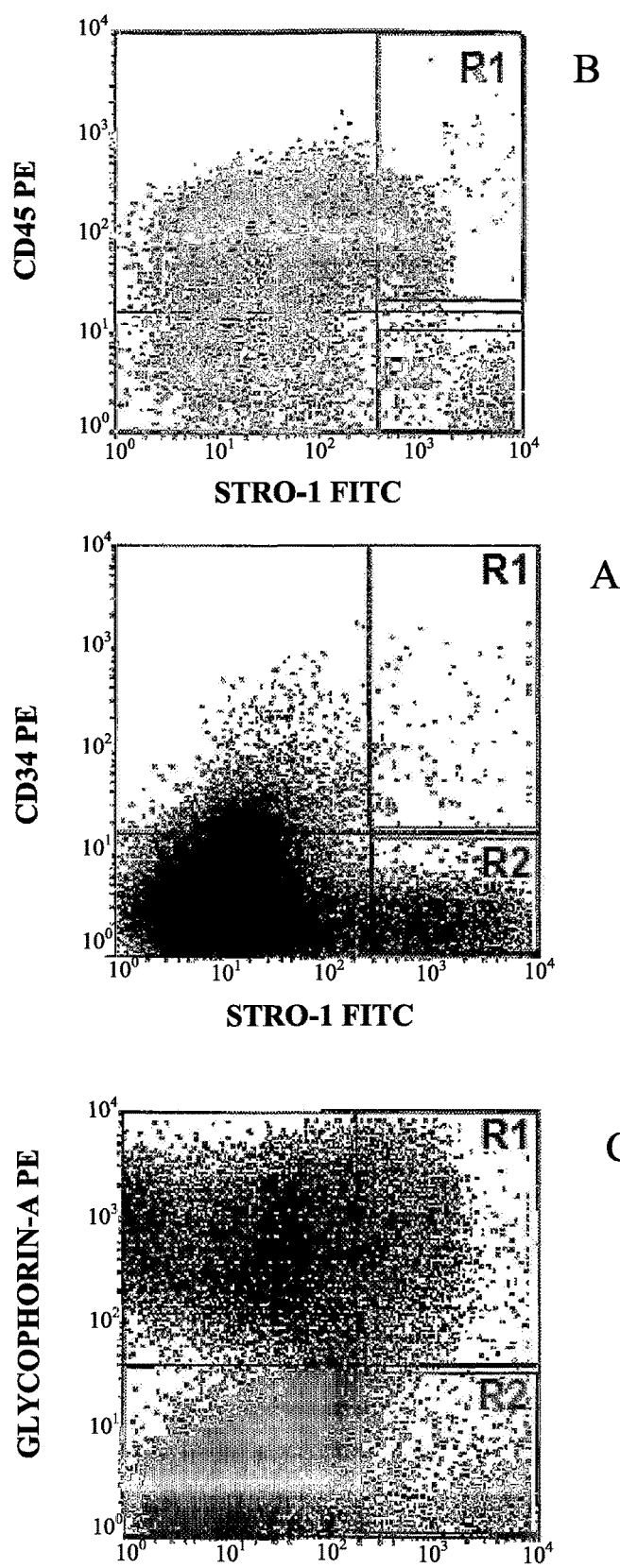

FIG. 6 Expression of CD34, CD45 and Glycophorin-A on STRO-1 positive bone marrow mononuclear cells. Representative histograms depicting typical dual-colour flow cytometric analysis profiles of STRO-1 positive bone marrow mononuclear cells isolated initially by magnetic activated sorting and co-stained with antibodies directed against CD34 (A), CD45 (B) or Glycophorin-A (C). The STRO-1 antibody was identified using a goat anti-murine IgM-fluorescein isothiocyanate while CD34, CD45 and Glycophorin-A were identified using a goat anti-murine IgG-phycoerythrin. The high expressing STRO-1 fraction which contained the clonogenic MPC population was isolated by fluorescence activated cell sorting based on regions R1 and R2.

Figure 7:
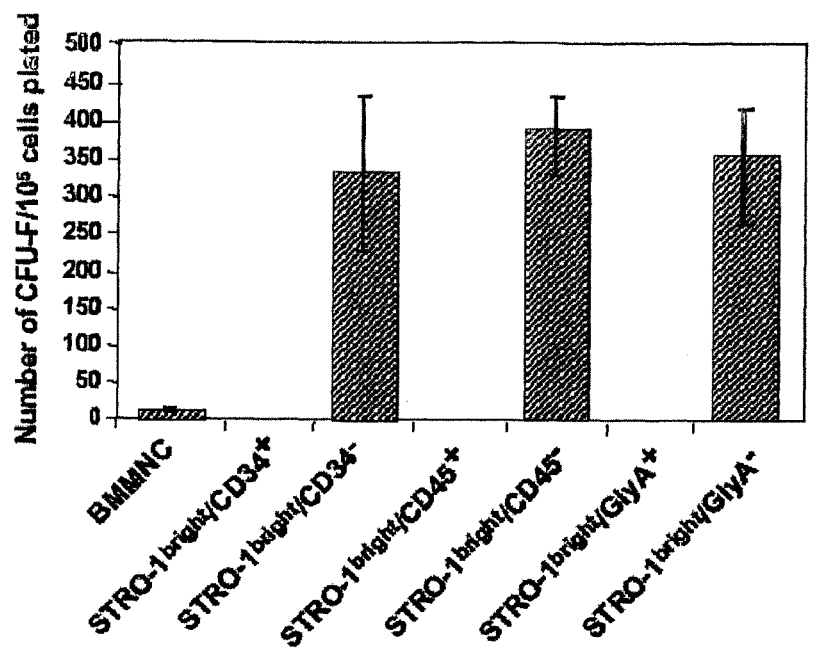
Figure 8A:
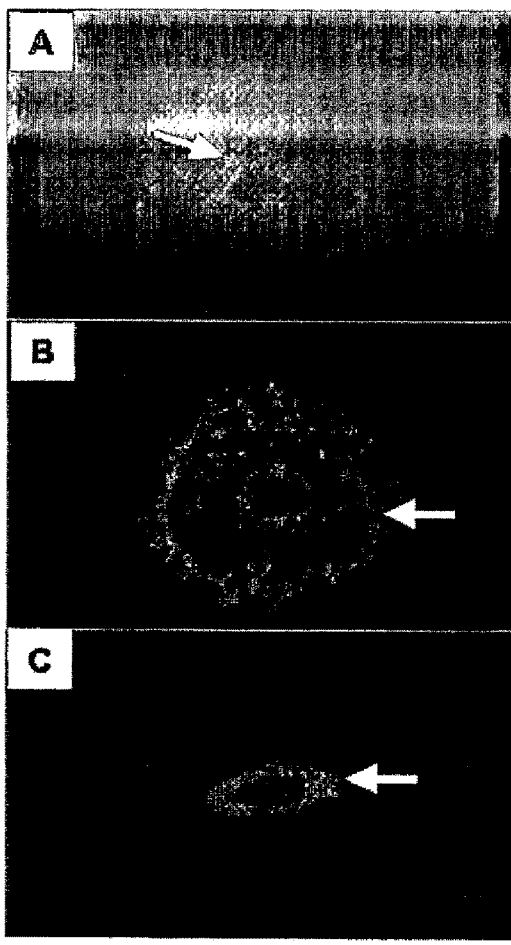
Figure 8A:
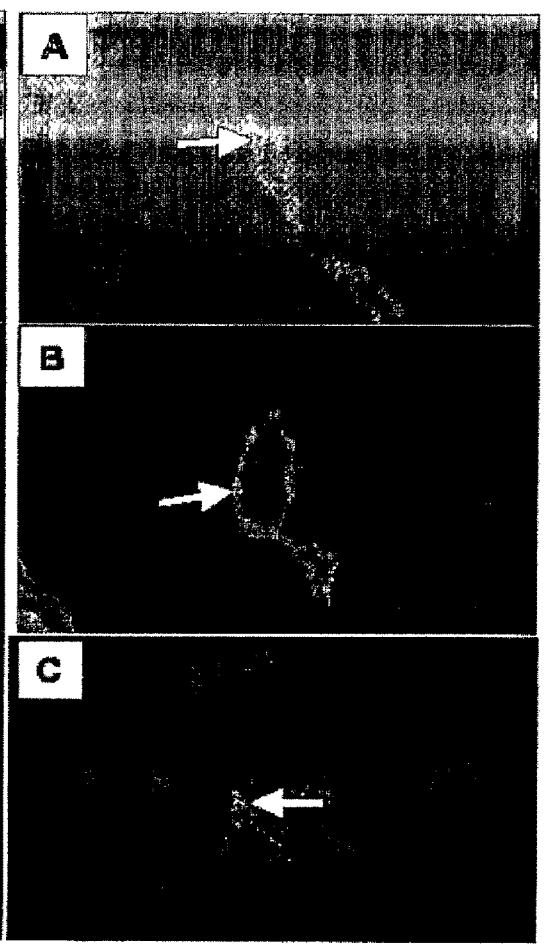
Figure 8B:
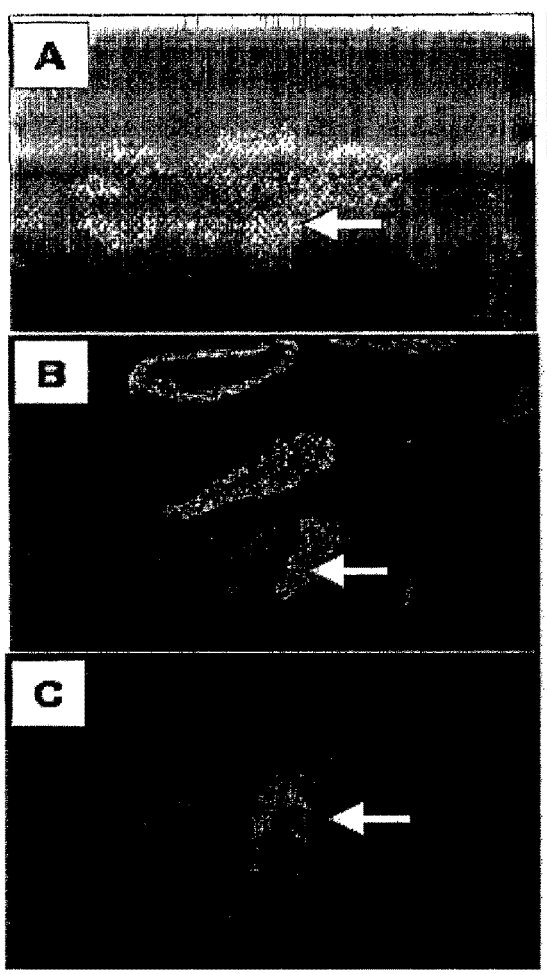
Figure 8B:
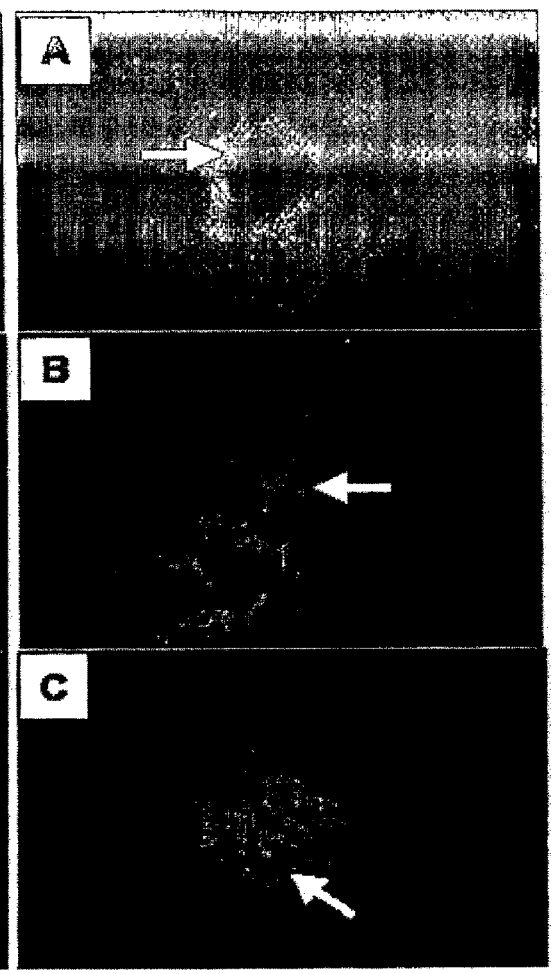
Figure 8C:
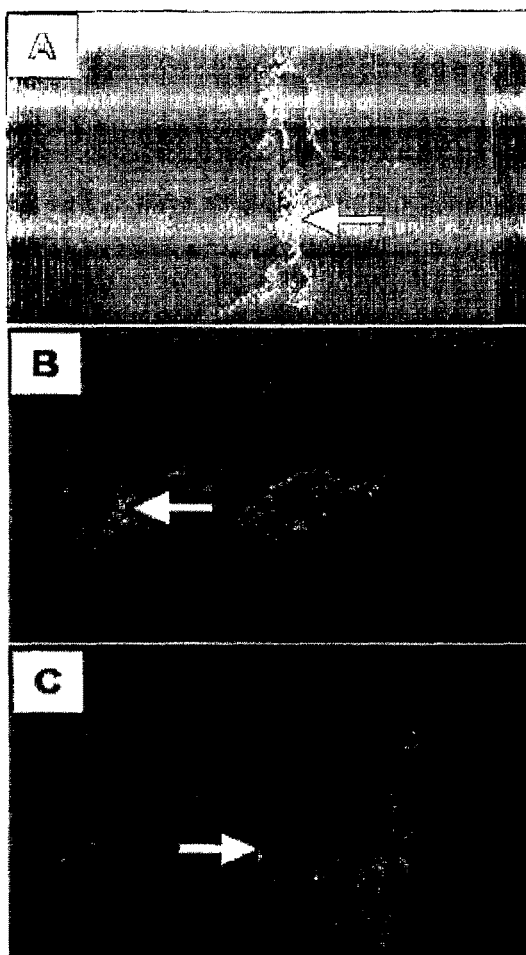
Figure 8C:
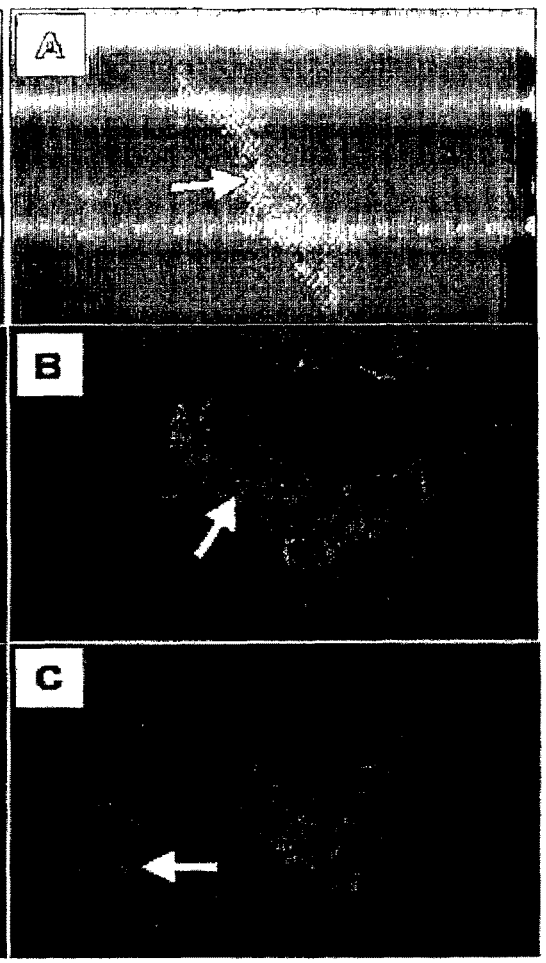
Figure 8D:
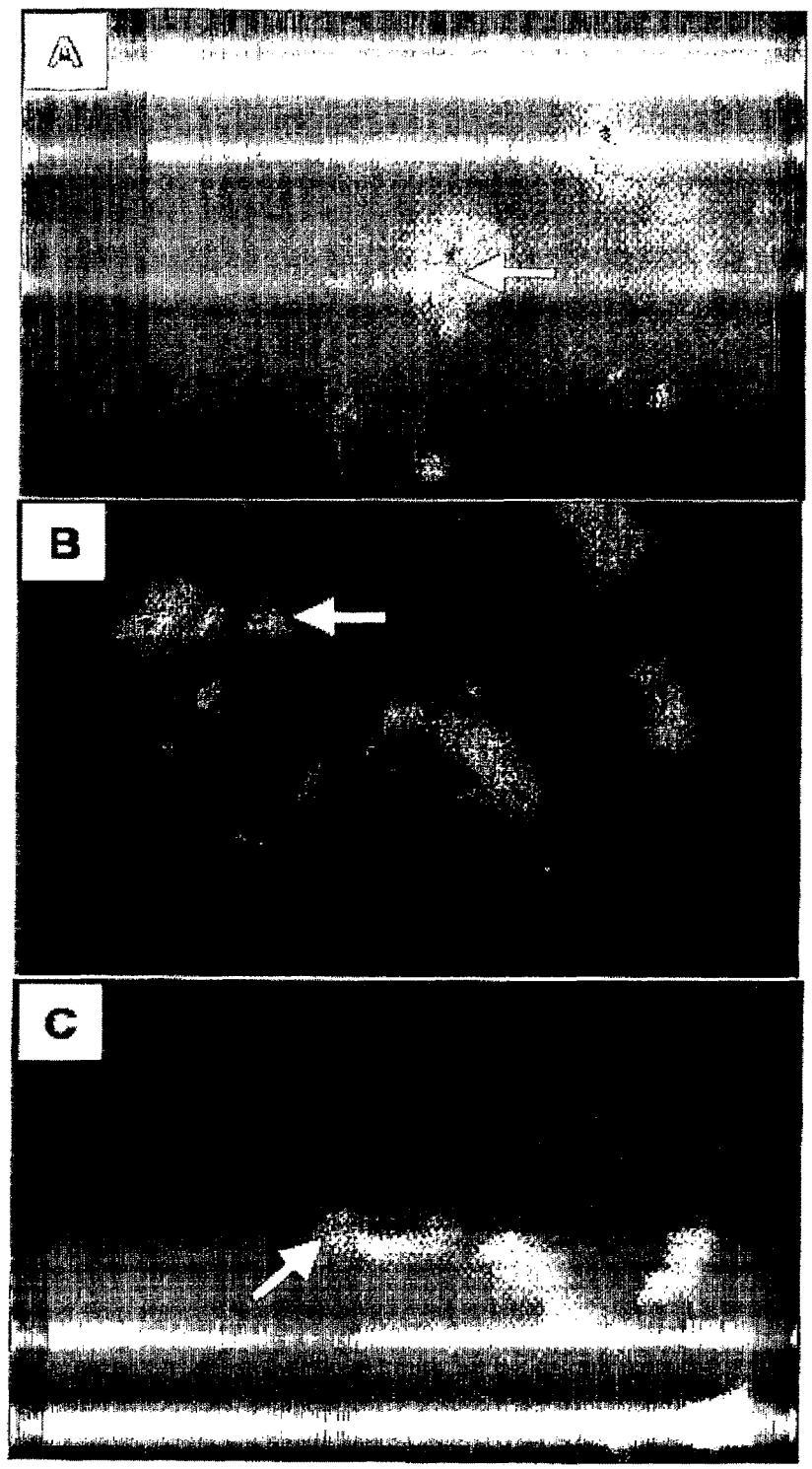

FIG. 7 Bone marrow MPC are STRO-1 bright, CD34 negative, CD45 negative and Glycophorin-A negative. The graph depicts the results of in vitro adherent colony formation assays performed for each of the different sorted STRO-1 bright populations selected by their co-expression or lack of either the CD34, CD45 or Gycophorin-A antigens, based on regions R1 and R2 as indicated in FIG. 6. These data are expressed as the mean incidence of colony-forming units for each cell fraction averaged from two separate experiments.

FIG. 8 Reactivity of perivascular makers in different human tissues. Dual-colour immunofluorescence staining demonstrating reactivity of (A) STRO-1 and CD146, (B) STRO-1 and alpha-smooth muscle actin, and (C) 3G5 and CD146, on blood vessels and connective tissue present on spleen, pancreas (FIG. 8A), brain, kidney (FIG. 8B), liver, heart (FIG. 8C) and skin (FIG. 8D) 20×. The STRO-1 and 3G5 antibodies were identified using a goat anti-murine IgM-Texas Red while CD 146 and alpha-smooth muscle actin were identified using a goat anti-murine or IgG-fluorescein isothiocyanate. Co-localization is indicated by overlaping areas of yellow and orange fluorescence (white arrows).

Figure 9:
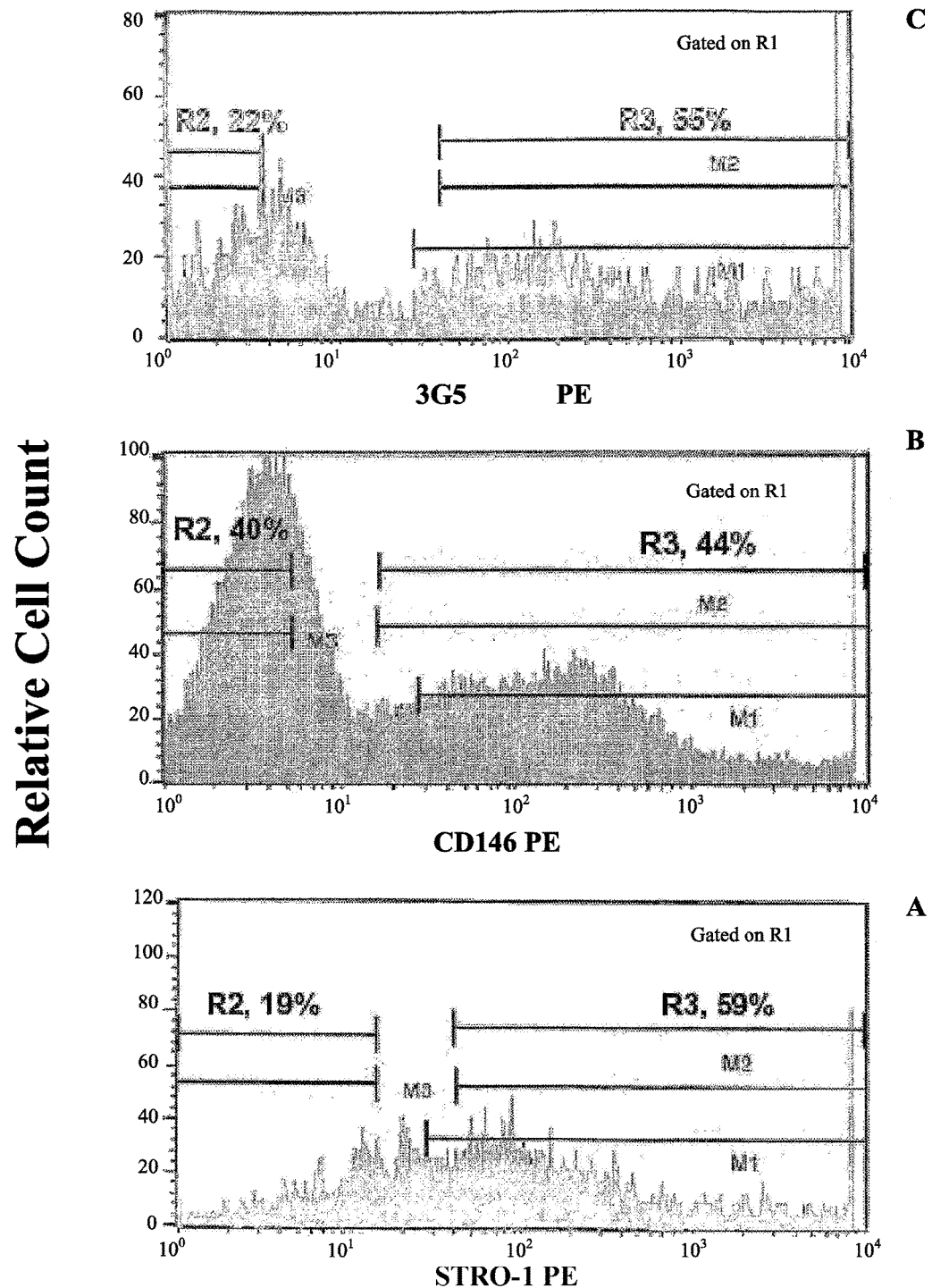

FIG. 9 Isolation of adipose-derived MPC by FACS. Representative flow cytometirc histograms depicting the expression of STRO-1(A), CD146 (B) and 3G5 ( C) in fresh preparations of peripheral adipose-derived single-cell suspensions generated following collagenase/dispase digestion as previously described (Shi and Gronthos 2003). The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

Figure 10:
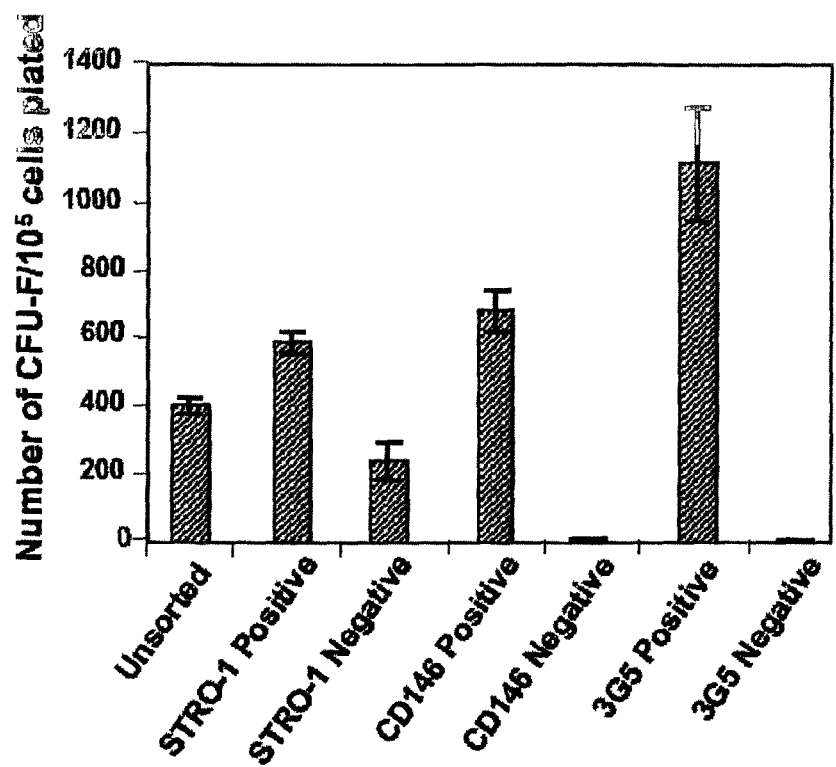

FIG. 10 Clonogenic adipose-derived MPC are positive for STRO-1/3G5/CD146. The bar graph depicts the number of clonogenic colonies retrieved from single cell suspensions of enzymatically digested human peripheral adipose tissue, following fluorescence activated cell sorting, based on their reactivity to antibodies that recognize STRO-1, CD146, and 3G5 (FIG. 9), then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

Figure 11:
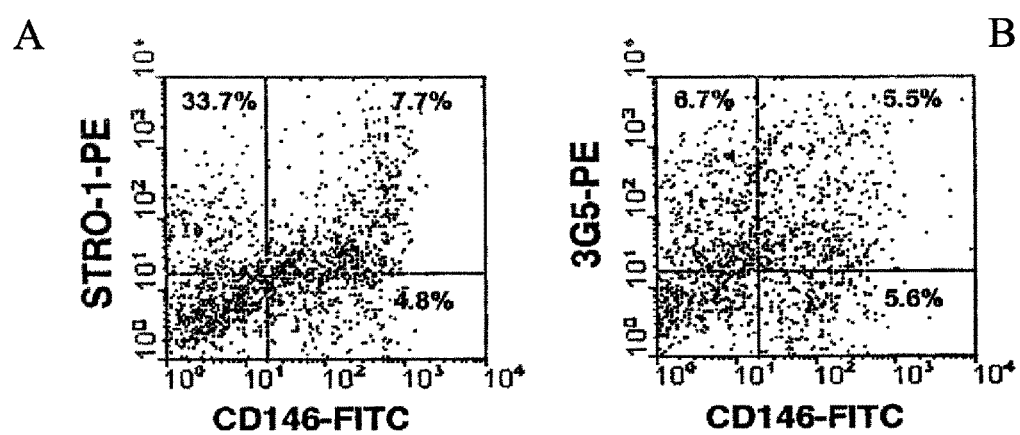

FIG. 11 Immunophenotypic analysis of adipose-derived MPC. Representative flow cytometric histograms depicting the co-expression of STRO-1 and CD 146 (A) and 3G5 and CD146 (B) in fresh preparations of peripheral adipose-derived single-cell suspensions generated following collagenase/dispase digestion. The STRO-1 and 3G5 antibodies were identified using a goat anti-murine IgM-phycoerythrin while CD146 was identified using a goat anti-murine IgG-fluorescein isothiocyanate. Approximately 60% and 50% of the CD146 positive cells co-express STRO-1 and 3G5, respectively. These data suggest that 10% or more of the CD164 positive cells co-express STRO-1 and 3G5.

Figure 12:
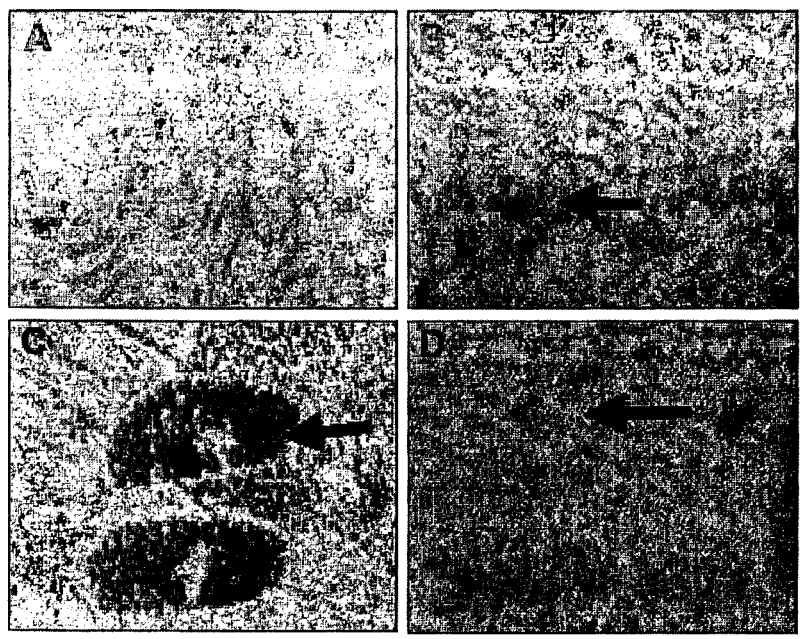

FIG. 12 Developmental potential of purified Adipocyte-derived MPC in vitro. Preparations of primary MPC cultures derived from STRO-1+/CD146+ adipose cells were re-cultured either in standard culture conditions (A), osteogenic inductive medium (B), Adipogenic inductive medium (C) or condrogenic conditions (D) as previously described Gronthos et al. 2003. Following two weeks of multi-differentiation induction, the adipocyte-derived MPC demonstrated the capacity to form bone (B; Alizarin positive mineral deposits), fat (C; Oil Red O positive lipid) and cartilage (D: collagen type II matrix).

Figure 13:
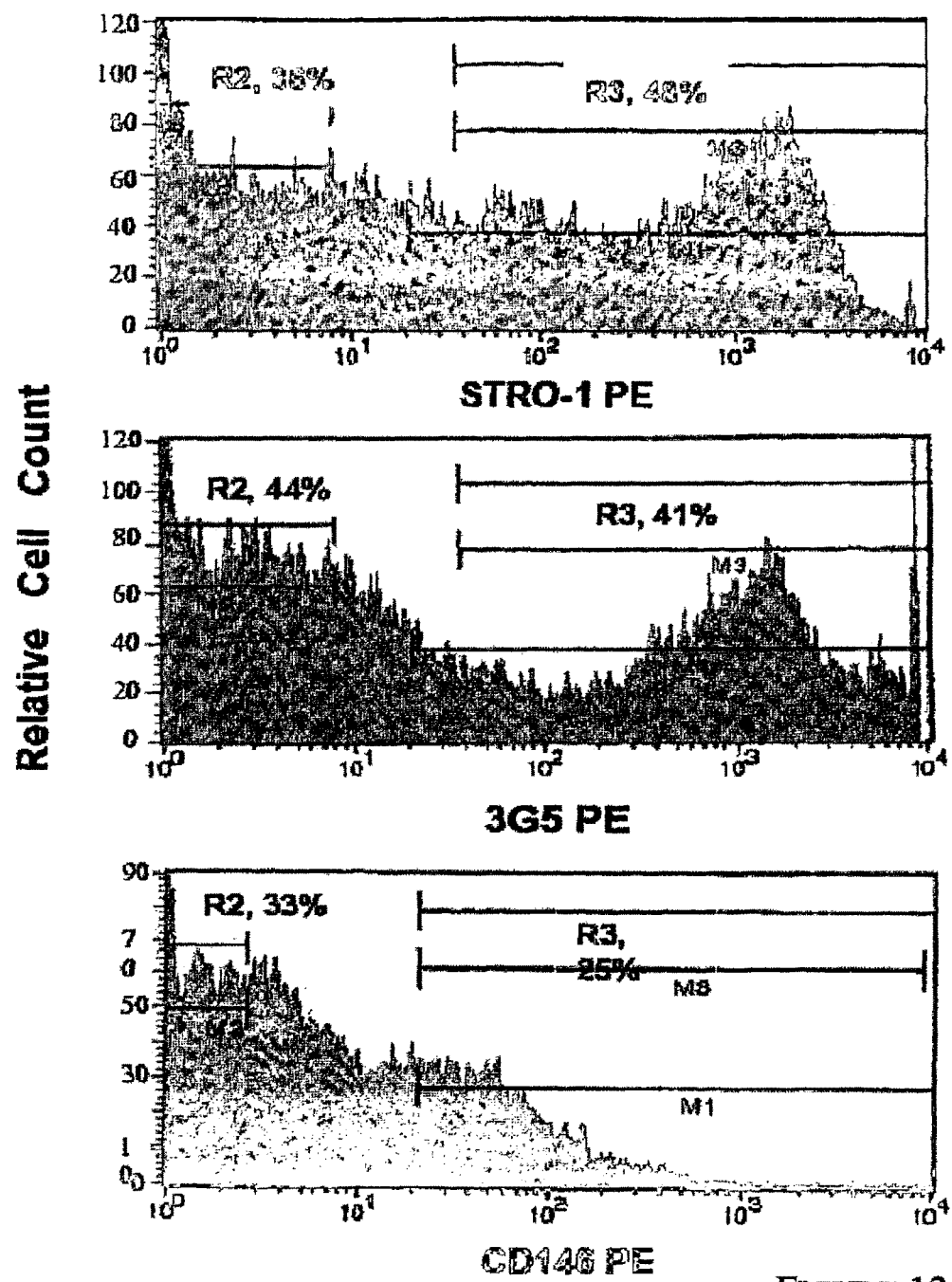

FIG. 13 Isolation of skin-derived MPC by FACS. Representative flow cytometirc histograms depicting the expression of STRO-1, CD146 and 3G5 in fresh preparations of full thickness skin-derived single-cell suspensions generated following collagenase/dispase digestion. The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

Figure 14:
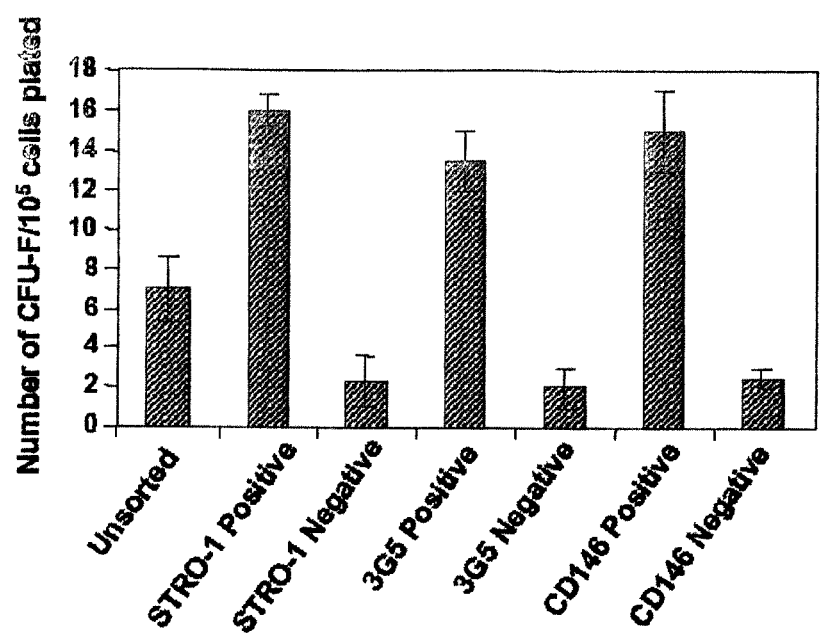

FIG. 14 Clonogenic skin-derived MPC are positive for STRO-1/3G5/CD146. The bar graph depicts the number of adherent colonies recovered from single cell suspensions of enzymatically digested human skin, following fluorescence activated cell sorting, based on their reactivity to antibodies that recognize STRO-1, CD146, and 3G5 (FIG. 6), then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

Figure 15:
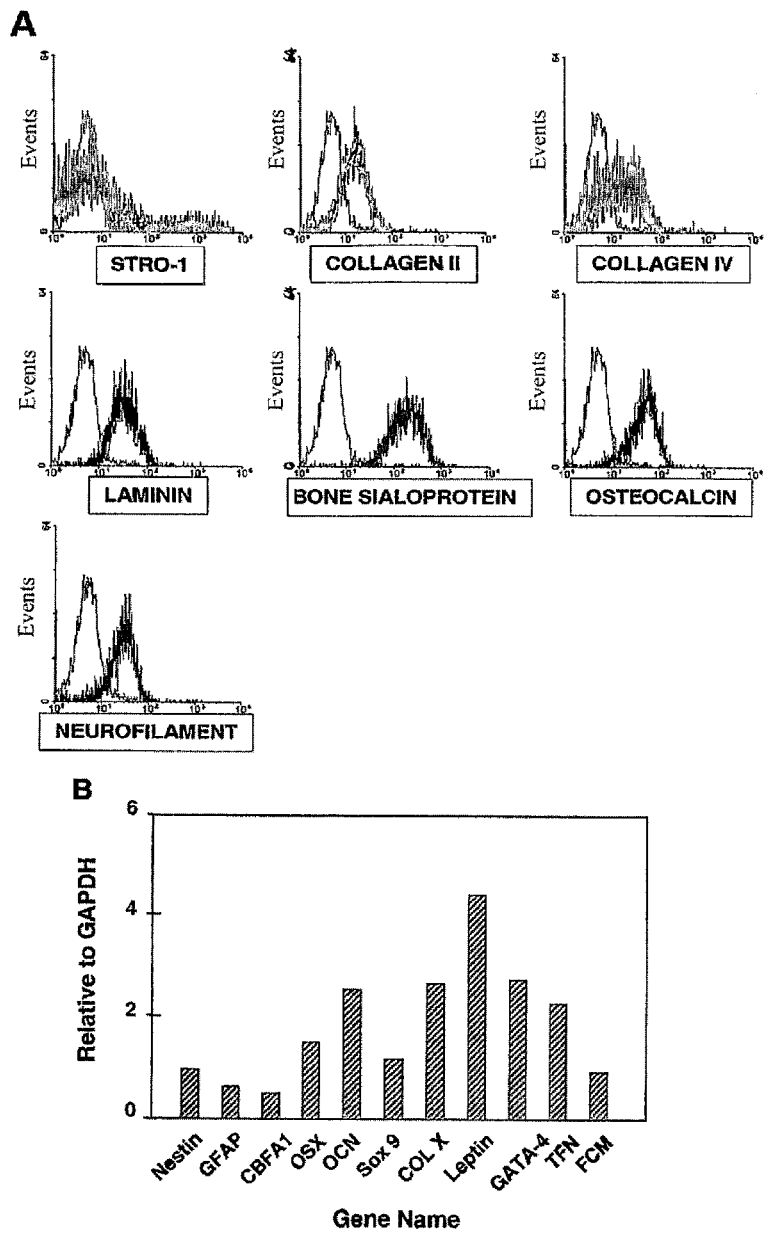

FIG. 15 A. Immunophenotypic expression pattern of ex vivo expanded bone marrow MPC. Single cell suspensions of ex vivo expanded bone marrow MPC were prepared by trypsin/EDTA treatment then incubated with antibodies identifying cell lineage-associated markers. For those antibodies identifying intracellular antigens, cell preparations were fixed with cold 70% ethanol to permeanbilize the cellular membrane prior to staining for intracellular markers. Isotype matched control antibodies were treated under identical conditions. Row cytometric analysis was performed using a COULTER EPICS instrument. The dot plots represent 5,000 listmode events indicating the level of fluorescence intensity for each lineage cell marker (bold line) with reference to the isotype matched negative control antibodies (thin line). B. Gene expression profile of cultured MPC. Single cell suspensions of ex vivo expanded bone marrow MPC were prepared by trypsin/EDTA treatment and total cellular RNA was prepared. Using RNAzolB extraction method total RNA was isolated and used as a template for cDNA synthesis, prepared using standard procedure. The expression of various transcripts was assessed by PCR amplification, using a standard protocol as described previously (Gronthos et at 2003). Primers sets used in this study are shown in Table 2. Following amplification, each reaction mixture was analysed by 1.5% agarose gel electrophoresis, and visualised by ethidium bromide staining. Relative gene expression for each cell marker was assessed with reference to the expression of the house-keeping gene, GAPDH, using ImageQuant software.

Figure 16:
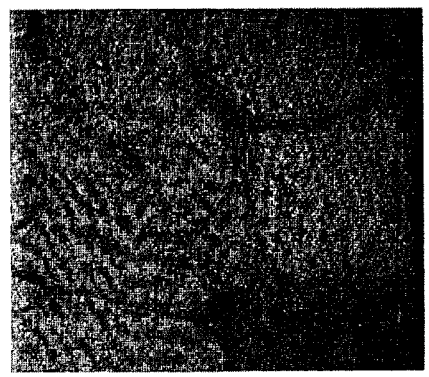

FIG. 16. Ex vivo expanded STRO-1$^{bri}$ MPC can develop into arterioles in vitro. Single cell suspensions of ex vivo expanded bone marrow STRO-1$^{bri}$ MPC were prepared by trypsin/EDTA treatment then plated into 48-well plates containing 200 µl of matrigel. The STRO-1$^{bri}$ MPC were plated at 20,000 cells per well in serum-free medium (Gronthos et al. 2003) supplemented with the growth factors PDGF, EGF, VEGF at 10 ng/ml. Following 24 hours of culture at 37° C. in 5% $CO_2$, the wells were washed then fixed with 4% paraformaldehyde. Immunohistochemical studies were subsequently performed demonstrated that the cord-like structures expressed alpha-smooth muscle actin identified with a goat-anti-murine IgG horse radish peroxidase antibody.

DETAILED DESCRIPTION OF THE ILLUSTRATED AND EXEMPLIFIED EMBODIMENTS OF THE INVENTION

The present invention relates to mesenchmal precursor cells, in particular those that may be present in the perivascular compartment of vascularised tissue. Such mesenchymal cells may be identified by the presence of the 3G5 surface marker, and perhaps additionally or separately by other early developmental markers such as CD146 (MUC18), VCAM-1 and STRO-1.

Precursor cells are early cells that are substantially at a pre-expansion stage of development. These are cells that have yet to differentiate to fully committed cells, however they need not be stem cells in a strict sense, in that they are necessarily able to differentiate into all types of cells. Partially differentiated precursor cells have a benefit in that they have a greater proliferative potential than stem cells.

The present precursor cells are somewhat differentiated in that they are committed to mesenchymal tissue, as opposed, for example, to haemopoietic tissues. It is evident from the data produced that the MPCs that have been isolated lack markers associated with haemopoietic cells such as CD34, and additionally their differentiation potential does not extend to haemopoietic lines. Additionally they need not necessarily have the potential to differentiate into all mesenchymal cell type, rather, they may be able to differentiate into one, two three or more cell types.

It is anticipated that these precursor cell harvested from the tissues concerned may be useful for regenerating tissue for cells types from which they have been sourced. Thus precursor cells isolated from heart may be reintroduced to regenerate heart tissue, however their potential need not be so limited, precursor cells isolated from one tissue type might be useful for regenerating tissue in another tissue type. The microenvironment in which an undifferentiated cell finds itself is known to exert an influence on the route of differentiation and therefore the reintroduction need not necessarily be tissue specific.

The data presented show that MPCs have been harvested and then re-introduced to produce bone and bone marrow and dentin and pulp respectively, in addition aterioles, cord like structures, have been produced after ex vivo expansion of isolated MPCs.

It is anticipated that a wide range of cells might be produced based on gene expression of markers characteristic for certain cell types. It is thus anticipated that under appropriate culture conditions the range of cell types that can be generated from the perivascular MPCs of the present invention include but are not limited to the following, osteoblast, odontoblast, dentin-producing, chondrocyte, tendon, ligament, cartilage, adipocyte, fibroblast, marrow stroma, osteoclast- and hematopoietic-supportive stroma, cardiac muscle, smooth muscle, skeletal muscle, pericyte, vascular, epithelial, glial, neuronal, astrocyte or oligodendrocyte cell.

One of the benefits of the finding that MPCs can be isolated from perivascular cells is that this greatly expands the range of source tissues from which MPCs can be isolated or enriched and there is no longer an effective restriction on the source of MPCs to bone marrow. The tissues from which these MPCs have been isolated in the exemplifications of this invention are human bone marrow, dental pulp cells, adipose tissue and skin. In addition in situ staining and histological studies have identified that MPC are present in the perivascular compartment of spleen, pancreas, brain, kidney, liver and heart. Given this wide and diverse range of tissue types where perivascular MPCs are present, it is proposed that MPC will also be present from an even wider range of tissue which may include, adipose tissue, teeth, dental pulp, skin, liver, kidney, heart, retina, brain, hair follicles, intestine, lung, spleen, lymph node, thymus, pancreas, bone, ligament, bone marrow, tendon, and skeletal muscle.

These precursor cells of the present invention are distinguished from other known MPCs in that they are positive for 3G5 or perhaps that they carry another perivascular markers. They can be isolated by enriching for an early developmental surface marker present on perivascular cells, in particular the presence of one or more of CD146(MUC18), VCAM-1 and alternatively or additionally high level expression of the marker recognised by the monoclonal antibody STRO-1. Alternatively or additionally enrichment may be carried out using 3G5.

Markers associated with perivascular cells may also be present on the MPCs, for example alpha smooth muscle actin (αSMA).

Other early developmental markers associated with MPCs may also be present. These may include but are not necessarily limited to the group consisting of THY-1, VCAM-1, ICAM-1, PECAM-1, CD49a/CD49b/CD29, CD49c/CD29, CD49d/CD29, CD29, CD61, integrin beta 5, 6-19, thrombomodulin, CD10, CD13, SCF, STRO-1bri, PDGF-R, EGF-R, IGF1-R, NGF-R, FGF-R, Leptin-R (STRO-2). Positive expression of one or more of these markers may be used in methods of enriching for MPCs from source tissue.

The MPCs of the present invention may also be characterised by the absence of markers present in differentiated tissue, and enrichment may be based on the absence of such markers.

Similarly it is preferred that the enriched cell populations are not of haemopoietic origin and thus it is preferred that these cells are not present. Markers characteristically identified as not present include but are not limited to CD34, CD45 and glycophorin A. Additional other markers for this purpose might include CD20 and CD19 (B lymphocyte markers), CD117 (c-kit oncoprotein) present on hemopoietic stem cells and angioblasts, CD14 (macrophage), CD3 and CD4 (T cells).

It may be desirable to use the relatively quiescent, directly enriched or isolated perivascular MCPs. Alternatively it has been discovered that expansion of the enriched population can be carried out and have the beneficial effect of resulting in much greater numbers of cells. The effect of expansion of the directly enriched pool of cells is, however, that some differentiation of the initial MCPs will occur. Expansion over a 5 week period might result in an increase of $10^3$ fold. Other periods might be chosen to expand the population to between $10^2$ to $10^5$ fold. This potential might be directed by culturing them is media containing cytokines and other factors directing the differentiation to a particular tissue type for example PDGF and VEGF forming smooth muscle alpha cords. These could then be introduce into a tissue with, for example, an insult to assist with repair. Alternatively it may be desired after expansion to re select cells on the basis of an early developmental marker, that might be STRO-$1^{bri}$ to increase the proportion of MPCs in the population.

It is found that an essentially pure population of MCPs is not necessary to provide for formation of differentiated cells to form desired tissue structures. The enriched population may have levels of MCPs of greater than about 0.001, 0.01, 0.02, 0.05, 0.1, 0.2, 0.5 or 1% or higher as a proportion of total cell numbers in the enriched population. This order of enrichment can be achieved by the use of a single marker for selection of the enriched MCP population. This is particularly so where the source tissue has an inherently high level of perivascular MCPs. It is found that considerably more 3G5 pos MCPs are present in certain tissue, for example dental pulp, than in bone marrow. Thus in bone marrow 3G5 positive MPCs constitute about 15% of MPC based on STR1$^{bri}$ colony forming cells, whereas in dental pulp that are found to constitue 65% and greater than 90% in fat and akin tissues. Expansion of the population and then re-enrichment using a single marker coung result in higher leves of MPCs, perhaps levels greaer than about 0.1, 0.5, 1, 2, 5 or 10%

Whilst it is considered desirable that a substantial proportion and preferably a majority of precursor cells are perivascular MPCs, it is not considered essential for certain forms of the invention for perivascular MPCs to be the sole precursor cell form. Other forms of precursors may also be present without unduly interfering with the capacity of the perivascular MPCs to undergo the desired differentiation. Such other forms may include haemopoietic precursors or non-perivascular MPCs, perhaps being negative for 3G5.

Certain forms of the present invention provide perivascular MPCs substantially free of endothelial cells. In that context substantially free might be considered to be less than about 5, 2, 1, or 0.1% endothelial cells. Alternatively the context might be an assessment that the enriched population is von Willebrand Factor negative.

It will be understood that recognition of cells carrying the cell surface markers that form the basis of the separation can be effected by a number of different methods, however, all of these methods rely upon binding a binding agent to the marker concerned followed by a separation of those that exhibit binding, being either high level binding, or low level binding or no binding. The most convenient binding agents are antibodies or antibody based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies may be attached to a solid support to allow for a crude separation. The separation techniques should maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS.

It is in the context of these methods that a cell be either negative or positive. The positive cells may either be low (lo) or a hi (bright) expresser depending on the degree to which the marker is present on the cell surface, the terms relate to intensity of fluoresence or other color used in the color sorting process of the cells. The distinction of lo and bri will be understood in the context of the marker used on a particular cell population being sorted.

The method of enriching for perivascular MPCs might include the step of making a first partially enriched pool of cells by enriching for the expression of a first of the markers, and then the step of enriching for expression of the second of the markers from the partially enriched pool of cells.

It is preferred that the method comprises a first step being a solid phase sorting step, based on recognition of one or more of the markers. The solid phase sorting step of the illustrated embodiment utilises MACS recognising high level expression of STRO-1. This then gives an enriched pool with greater numbers of cells than if a high accuracy sort was used as a first step. If for example FACS is used first, many of the precursor cells are rejected because of their association with other cells. A second sorting step can then follow using an accurate separation method. This second sorting step might involve the use of two or more markers. Thus in the illustrated embodiment two colour FACS is used to recognise high level expression of the antigen recognised by STRO-1 as wells as the expression of CD146. The windows used for sorting in the second step can be more advantageously adjusted because the starting population is already partially enriched.

The method of enriching for perivascular MPCs might also include the harvesting of a source of the stem cells before the first enrichment step using known techniques. Thus the tissue will be surgically removed. Cells comprising the source tissue will then be seprated into a so called single cells suspension. This separation may be achieved by physical and or enzymic means.

The preferred source of such perivascular MPCs is human, however, it is expected that the invention is also applicable to animals, and these might include agricultural animals such as cows, sheep, pigs and the like, domestic animals such as dogs, laboratory animals such as mice, rats, hamsters, and rabbits or animals that might be used for sport such as horses.

In a further form the invention might be said to reside a method of generation tissue in a mammal comprising the step of enriching a population of precursor cells as in the first aspect of the invention, and introducing the enriched population into the mammal, and allowing the enriched population to generate the tissue in the mammal.

Another potential use for enriched cells of the present invention is as a means of gene therapy, by the introduction of exogenous nucleic acids for expression of therapeutic substances in the tissue types concerned.

In the context of the present invention the term isolated cell may mean that perivascular MPCs comprise at least 30, 40, 50, 60, 70, 80, or 95% of total cells of the population in which they are present.

EXAMPLE 1

Isolation and Expansion of Precursor Cells

Stem cell niches identified in a number of different adult tissues including skin, hair follicles, bone marrow, intestine, brain, pancreas and more recently dental pulp, are often highly vascularized sites.[1] The maintenance and regulation of normally quiescent stem cell populations is tightly controlled by the local microenvironment according to the requirements of the host tissue.[2,3] Both the supportive connective tissues of bone marrow and dental pulp contain stromal stem cell populations with high proliferative potentials capable of regenerating their respective microenvironments with remarkable fidelity, including the surrounding mineralized structures of bone and dentin.[4,5] In the postnatal organism, bone marrow stroma exists as a loosely woven, highly vascularized tissue that supports and regulates hematopoiesis.[6-8] At a time when many tissues have lost or decreased their ability to regenerate, adult bone marrow retains a capacity for continuous renewal of haematopoietic parenchymal tissue and is responsible for remodeling the adjoining bone surfaces.[9,10] In contrast, the inner pulp chamber of teeth is comprised of a non-hematopoietic, compact fibrous tissue, infiltrated by a microvascular network, that is entombed by mineralized dentin.[11-13] Following tooth maturation, dental pulp becomes relatively static, acting only in a reparative capacity in response to a compromised dentin matrix caused by insults such as caries or mechanical trauma.

Precursors of functional osteoblasts (BMSSCs: bone marrow stromal stem cells) and odontoblasts (DPSCs: dental pulp stem cells), both forms of MPCs identified by their source tissue, were initially identified by their capacity to form clonogenic cell clusters in vitro, a common feature amongst different stem cell populations.[4,14-18] The progeny of ex vivo expanded BMSSCs and DPSCs share a similar gene expression profile for a variety of transcriptional regulators, extracellular matrix proteins, growth factors/receptors, cell adhesion molecules, and some, but not all lineage markers characteristic of fibroblasts, endothelial cells, smooth muscle cells and osteoblasts.[4,19] However, previous studies have documented that individual BMSSC colonies demonstrate marked differences in their proliferation rates in vitro and developmental potentials in vivo.[5,14,20] Similar to these findings, we have recently observed comparable levels of heterogeneity in the growth and developmental capacity of different DPSC colonies.[21] Together, these studies infer a hierarchical arrangement of stromal precursor cells residing in bone marrow and dental pulp, headed by a minor population of highly proliferative pluripotential stem cells that give rise to committed bi- and uni-potential progenitor cell populations.[22]

Despite our extensive knowledge about the properties of cultured BMSSCs and DPSCs, we still do not know if their in vitro characteristics are an accurate portrait of their true gene expression patterns and developmental potentials in situ. In addition, it is not formally known if all of the colony-forming cells within each tissue are derived from one pluri-potent stem cell pool or whether they arise from committed progenitors belonging to distinct lineages. There is also a lack of information regarding the precise anatomical location of BMSSCs and DPSCs in their respective tissues. This is mainly attributed to the rarity of stem cells and the absence of specific markers that identify different developmental stages during osteogenesis and odontogenesis, particularly for primitive subpopulations. It has previously been hypothesized that one possible niche for precursors of osteoblasts and odontoblasts may be the microvasculature networks of bone marrow and dental pulp, respectively.[23,24]

Materials and Methods

Tissue Samples

Iliac crest-derived bone marrow mononuclear cells (BMMNCs), from normal human adult volunteers were obtained under guidelines set by the Royal Adealaide Hospital Human Ethics Committee. Normal human impacted third molars were collected from young adults the University of Adelaide Dental Clinic Research under approved guidelines set by the University of Adelaide Human Ethics Committee, respectively. Discarded full thickness skin and peripheral adipose tissue were obtained from routine plastic surgery procedures from the Skin Cell Engineering Laboratory, under the guidelines set by the Royal Adelaide Hospital Human Ethics Committee. The pulp tissue was separated from the crown and root as previously described.[4] Single cell suspensions of dental pulp, skin and adipose tissue were prepared by enzymatic digestion in a solution of 3 mg/ml collagenase type I (Worthington Biochem, Freehold, N.J.) and 4 mg/ml dispase (Boehringer Mannheim, GMBH, Germany) for one to three hours at 37° C. Single cell suspensions were obtained by passing the cells through a 70 μm strainer (Falcon, BD Labware, Franklin Lakes, N.J.). Cell (0.01 to $1\times10^5$/well) preparations of bone marrow, dental pulp, skin and adipose were then used for either, immunolselection, RNA extraction, or direct culture in 6-well plates (Costar, Cambridge, Mass.) as described below.

Other human tissue specimens (Brain, liver, heart, kidney, lung, spleen, thymus, lymph node, pancreas, skin) were obtained from autopsies carried out at the Royal Adelaide Hospital during routine pathological examinations under approved guidelines set by the Royal Adelaide Hospital Human Ethics Committee. Small specimens approximately 0.5 cm² of each tissue type were placed into Tissue-Tek II cryomoulds 25 mm×20 mm×5 mm (Miles Laboratories; Naperville, Ill.) and embedded with O.C.T. compound medium (Miles Laboratories) by immersion into a 150 ml to 200 ml pyrex glass beaker of iso-pentane (BDH Chemicals, Poole, England) pre-cooled by suspending a glass beaker into a bath of liquid nitrogen. The isopentane has cooled when the bottom of the glass is white. The frozen sections were immediately stored at −30° C. Frozen sections of nerve and muscle tissue were obtained from the Histopathology Department of the I.M.V.S., South Australia and sections of foreskin were obtained from the Immunology Department of the I.M.V.S., South Australia. Sections of formalin fixed, paraffin embedded human foetal limb (52 days) were kindly provided by Dr. T. J. Khong from the Department of Histopathology, Women's and Children's Hospital, Adelaide, South Australia.

Colony Efficiency Assay and Culture

Single cell suspensions were plated at low plating densities (between 1,000 and 10,000 cells per well, as triplicates in six well plates) to assess colony-forming efficiency of different immunoselected cell fractions. The cells were cultured in alpha-Modification of Eagle's Medium supplemented with 20% foetal calf serum, 2 mM L-Glutamine, 100 μM L-ascorbate-2-phosphate, 100 U/ml penicillin and 100 μg/ml streptomycin at 37° C. in 5% $CO_2$. Day 14 cultures were fixed with 4% formalin, and then stained with 0.1% toluidine blue. Aggregates of equal to or greater than fifty cells were scored as clonogenic colonies equivalent to colony forming units-fibroblastic (CFU-F).

Magnetic-Activated Cell Sorting (MACS)

This procedure is a modification of that described elsewhere.[25] Briefly, approximately $1\times10^8$ BMMNCs were incubated with STRO-1bri supernatant (murine anti-human BMSSCs, IgM)[29] (1/2) for 1 hour on ice. The cells were then washed with PBS/5% FBS and resuspended in a 1/50 dilution of biotinylated goat anti-mouse IgM (μ-chain specific; Caltag Laboratories, Burlingame, Calif.) for 45 minutes on ice. After washing, the cells were incubated with streptavidin microbeads (Miltenyi Biotec, Bergisch Gladbach, F. R. G.) for 15 minutes on ice, then separated on a Mini MACS magnetic column (Miltenyi Biotec) according to the manufacturers recommendations.

Fluorescence Activated Cell Sorting (FACS)

STRO-1bri MACS isolated cells were incubated with a streptavidin-FITC conjugate (1/50; CALTAG Laboratories) for 20 minutes on ice then washed with PBS/5% FBS. Single-color fluorescence activated cell sorting (FACS) was performed using a FACStar$^{PLUS}$ flow cytometer (Becton Dickinson, Sunnyvale, Calif.). Dual color-FACS analysis was achieved by incubating MACS-isolated STRO-1$^{bri}$ BMMNCs with saturating (1:1) levels of CC9 antibody supernatant (mouse anti-human CD146/MUC-18/MelCAM, $IgG_{2as}$ Dr. Stan Gronthos) for one hour on ice. After washing with PBS/5% FBS, the cells were incubated with a second label goat anti-mouse $IgG_2a$ (γ-chain specific) phycoerythrin (PE) conjugate antibody (1/50, CALTAG Laboratories) for 20 minutes on ice. The cells were then sorted using the automated cell deposition unit (ACDU) of a FACStar$^{PLUS}$ flow cytometer. Limiting dilution assay: seeded 1, 2, 3 4, 5, & 10 cells per well, 24 replicates, cultured in serum-deprived medium for 10 days as previously described[26]. Similarly, freshly prepared unfractionated BMMNCs were incubated with CC9 ($IgG_{2a}$) and 3G5 (IgM) antibodies or isotype-matched negative control antibodies for one hour on ice. After washing with PBS/5% FBS, the cells were incubated with a second label goat anti-mouse $IgG_{2a}$ (γ-chain specific) phycoerythrin (PE) and IgM (1/50; CALTAG Laboratories) conjugated antibodies for 30 minutes on ice. Cells were washed in PBS/%5 FBS prior to being analysed using a FACStar$^{PLUS}$ flow cytometer. Positive reactivity for each antibody was defined as the level of fluorescence greater than 99% of the isotype matched control antibodies.

Flow Cytometric Analysis

Single cell suspensions of ex vivo expanded bone marrow MPC were prepared by trypsin/EDTA treatment then incubated with neat STRO-1 supernatant or antibodies identifying different cell lineage-associated markers (10 μg/ml) for one hour on ice. The cells were then washed in PBS/5% FBS then incubated either with a goat anti-murine IgM-phycoerythrin (1/50, SouthernBiotechnologies), goat anti-murine or anti-rabbit IgG-phycoerythrin (Caltag Laboratories). For those antibodies identifying intracellular antigens, cell preparations were permeanbilize the cellular membrane prior to staining for intracellular markers. Isotype matched control antibodies were treated under identical conditions. Flow cytometric analysis was performed using a COULTER EPICS instrument. The dot plots represent 5,000 listmode events indicating the level of fluorescence intensity for each lineage cell marker with reference to the isotype matched negative control antibodies.

Immunhistochemistry

Human tissue sections (μm) were de-waxed in xylene and rehydrated through graded ethanol into PBS. Frozen tissue sections (μm) and cytospin preparations were fixed with cold acetone at −20° C. for 15 minutes then washed in PBS. The samples were subsequently treated with PBS containing 1.5% of hydrogen peroxide for 30 minutes, washed then blocked with 5% non-immune goat serum for 1 hour at room temperature. Samples were incubated with primary antibodies for 1 hour at room temperature. Antibodies used: Mouse (IgG$_1$ & IgC$_{2a}$) controls (Caltag, Burlingame, Calif.); Rabbit (Ig) control, 1A4 (anti-α smooth muscle actin, IgG$_1$), 2F11 (anti-neurofilament, IgG$_1$), F8/86 (murine anti-von Willebrand Factor, IgG$_1$) (Dako, Carpinteria, Calif.); STRO-1; CC9 (anti-CD146); LF-151 (rabbit anti-human dentinsialoprotein; Dr. L. Fisher, NIDCR/NIH, MD). Working dilutions: rabbit serum (1/500), monoclonal supernatants (1/2) and purified antibodies (10 μg/ml). Single staining was performed by incubating the samples with the appropriate secondary antibody, biotinylated goat anti-mouse IgM, IgG$_1$, IgG$_{2a}$ or biotinylated goat anti-rabbit for one hour at room temperature (Caltag Laboratories). Avidin-Peroxidase-complex and substrate were then added according to the manufacturer instructions (Vectastain ABC Kit standard, Vector Laboratories). Samples were counterstained with hematoxylin and mounted in aqueous media. Dual-fluorescence labeling was achieved by adding the secondary antibodies, goat anti-mouse IgM-Texas Red and IgG-FITC (CALTAG Laboratories), for 45 minutes at room temperature. After washing the samples were mounted in VECTASHIELD fluorescence mountant.

Immunomagnetic Bead Selection

Single cell suspensions of dental pulp tissue were incubated with antibodies reactive to STRO-1 (1/2), CD146 (1/2), or 3G5 (1/2) for 1 hour on ice. The cells were washed twice with PBS/1% BSA then incubated with either sheep anti-mouse IgG-conjugated or rat anti-mouse IgM-conjugated magnetic Dynabeads (4 beads per cell: Dynal, Oslo, Norway) for 40 minutes on a rotary mixer at 4° C. Cells binding to beads were removed using the MPC-1 magnetic particle concentrator (Dynal) following the manufactures recommended protocol.

Matrigel-Arteriole Assay

Single cell suspensions of ex vivo expanded bone marrow STRO-1$^{bright}$ MPC were prepared by trypsin/EDTA treatment then plated into 48-well plates containing 200 μl of matrigel. The STRO-1$^{bright}$ MPC were plated at 20,000 cells per well in serum-free medium (Gronthos et al. 2003) supplemented with the growth factors PDGF, EGF, VEGF at 10 ng/ml. Following 24 hours of culture at 37° C. in 5% $CO_2$, the wells were washed then fixed with 4% paraformaldehyde. Immunohistochemical studies were subsequently performed for alpha-smooth muscle actin identified with a goat-anti-murine IgG horse radish peroxidase antibody/Vectastaining Kit as described above.

Osteogenic, Adipogenic and Chondrogenic Differentiation of MPC In Vitro

Single cell suspensions of ex vivo expanded adipose-derived MPC were cultured in αMEM supplemented with 10% FCS, 100 μM L-ascorbate-2-phosphate, dexamethasone 10$^{-7}$M and 3 mM inorganic phosphate previously shown to induce bone marrow MPC to form a mineralized bone matrix in vitro (Gronthos et al., 2003). Mineral deposits were identified by positive von Kossa staining. Adipogenesis was induced in the presence of 0.5 mM methyl-isobutylmethylxanthine, 0.5 μM hydrocortisone, and 60 μM indomethacin as previously described (Gronthos et al. 2003). Oil Red O staining was used to identify lipid-laden fat cells. Chondrogenic differentiation was assessed in aggregate cultures treated with 10 ng/ml TGF-β3 as described (Pittenger et al., 1999)

In vivo Transplantation Studies

Approximately 5.0×10$^6$ of ex vivo expanded cells derived from either STRO-1$^{bri}$/CD146$^+$ BMSSCs or CD 146$^+$ DPSCs were mixed with 40 mg of hydroxyapatite/tricalcium phosphate (HA/TCP) ceramic powder (Zimmer Inc, Warsaw, Ind.) and then transplanted subcutaneously into the dorsal surface of 10-week-old immunocompromised beige mice (NIH-bg-nu-xid, Harlan Sprague Dawley, Indianapolis, Ind.) as previously described.[4] These procedures were performed in accordance to specifications of an approved animal protocol (NIDCR #00-113).

Reverse Transcription-polymerase Chain Reaction.

Total RNA was prepared from STRO-1$^{BRT}$/CD146$^+$ sorted BMMNCs, and control cells (primary BMSSC cultures grown in the presence of 10$^{-7}$ M dexamethasone for three weeks) using RNA STAT-60 (TEL-TEST Inc. Friendswood Tex.). First-strand cDNA synthesis was performed with a first-strand cDNA synthesis kit (GIBCO BRL, Life Technologies) using an oligo-dT primer. First strand cDNA (2 μl) was added to 46 μl of a 1×PCR master reaction mix (Roche Diagnostics, Gmbh Mannheim Germany) and 10 pMol of each human specific primer sets: CBFA1 (632 bp, and three smaller alternative splice variants)[27] sense 5'-CTATGGAGAGGACGCCACGCCTGG-3' [SEQ ID NO. 1], antisense, 5'-CATAGCCATCGTAGCCTTGTCCT-3' [SEQ ID NO. 2]; osteocalcin (310 bp)[4] sense, 5'-CATGAGAGCCCTCACA-3' [SEQ ID NO. 3], antisense, 5'-AGAGCGACACCCTAGAC-3' [SEQ ID NO. 4]; GAPDH (800 bp)[4] sense, 5'-AGCCGCATCTTCTTTT-GCGTC-3' [SEQ ID NO. 5]; antisense 5'-TCATATTTG-GCAGGTTTTTCT-3' [SEQ ID NO. 6]. The reactions were incubated in a PCR Express Hybaid thermal cycler (Hybaid, Franklin, Mass.) at 95° C. for 2 minutes for 1 cycle then 94° C./(30 sec), 60° C./(30 sec), 72° C./(45 sec) for 35 cycles, with a final 7 minute extension at 72° C. Following amplification, each reaction was analyzed by 1.5% agarose gel electrophoresis, and visualized by ethidium bromide staining.

RESULTS

BMSSCs and DPSCs express vascular associated antigens STRO-1 and CD146 in vivo.

Figure 1:
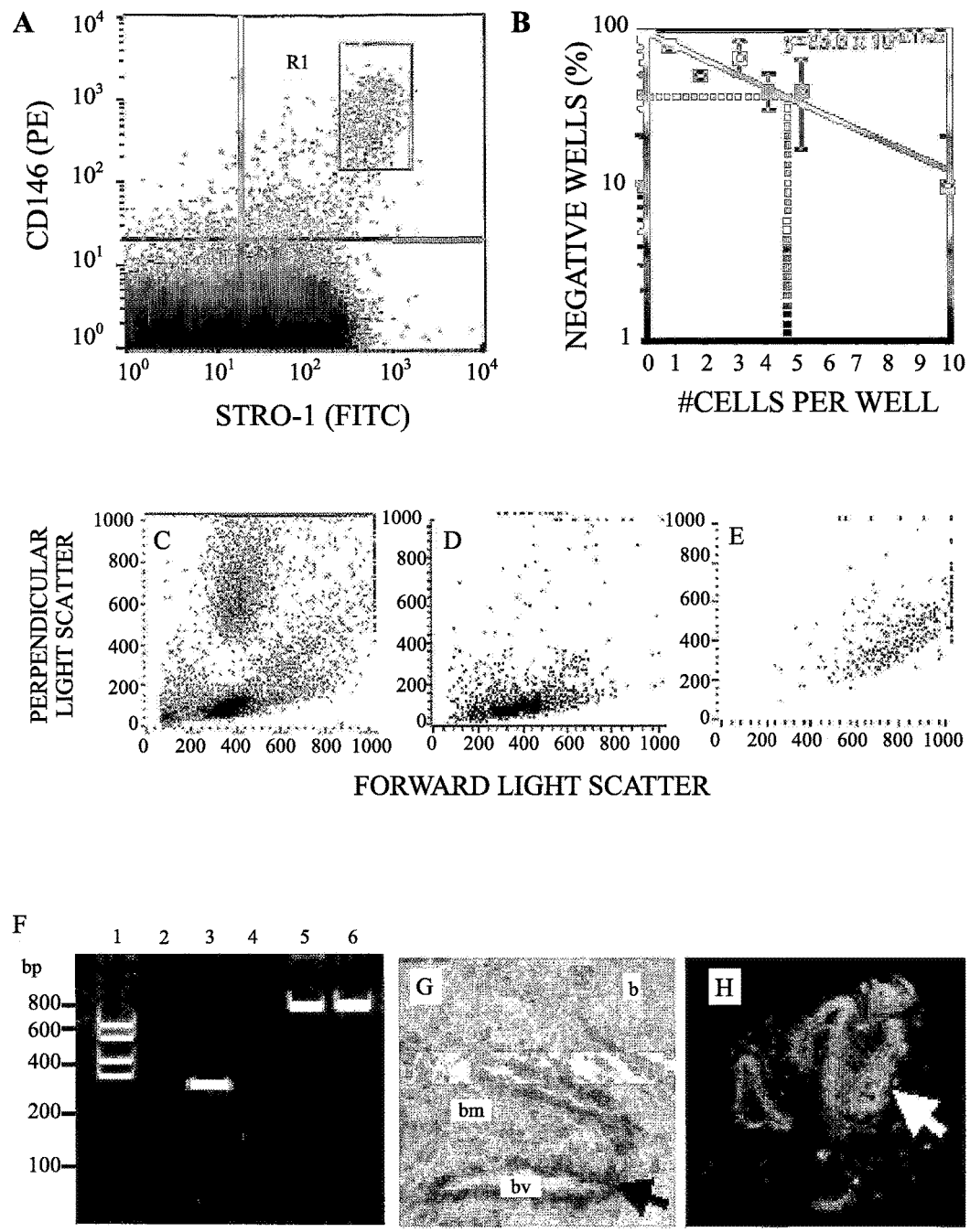
FIG. 1. Properties of STRO-1$^+$ MACS-isolated cells co-labeled with anti-CD146 (CC9). (A) Sort region, R1, represents the double positive STRO-1$^{BRT}$/CD146$^+$ population. (B) The incidence of clonogenic cell colonies (>50 cells) based on STRO-1$^{BRT}$/CD146$^+$ expression was determined by limiting dilution analysis of 24 replicates per cell concentration using Poisson distribution analysis from 5 independent experiments. Forward (size) and perpendicular (granularity) light scatter characteristics of BMMNCs (C), STRO-1$^{int}$/CD146$^-$ cells (D) and STRO-1$^{BRT}$/CD146$^+$ cells (E). (F) RT-PCR analysis of STRO-1$^{BRT}$/CD146$^+$ sorted marrow cells for CBFA1 (lane 2), osteocalcin (lane 4) and GAPDH (lane 6) transcripts. Control cells (BMSSC cultures grown in the presence of dexamethasone) expressing CBFA1 (lane 1), osteocalcin (lane 3), and GAPDH (lane 5) is also shown. Reaction mixes were subjected to electrophoresis on a 1.5% agarose gel and visualised by ethidium bromide staining. (G) In situ expression of CD 146 on blood vessel (bv) walls (arrow) in human bone marrow (bm)

We have previously demonstrated the efficacy of magnetic activated cell sorting (MACS), to isolate and enrich for all detectable clonogenic colonies from aspirates of human marrow, based on their high expression of STRO-1 antigen.[25,26] To further characterize BMSSCs we incubated the STRO-1$^{bri}$ MACS isolated cells with another monoclonal antibody, CC9,[28] that recognizes the cell surface antigen CD146, also known as MUC-18, Mel-CAM and Sendo-1, that is present on endothelial and smooth muscle cells. These studies determined that CC9, selectively bound the STRO-1 bright expressing fraction (STRO-1$^{BRT}$) from the total STRO-1$^+$ population by dual-color FACS analysis (FIG. 1A). Cloning efficiency assays using Poisson distribution statistics, yielded a marked increase in the incidence of BMSSCs (1 colony per 5 STRO-1$^{BRT}$/CD146$^+$ cells plated), and achieved a 2×10$^3$ fold enrichment of the clonogenic colony population when compared to unfractionated marrow (FIG. 1B). No colony formation could be detected in STRO-1$^{BRT}$/CD146$^-$ cell fraction (data not shown).

The light scatter properties of STRO-1$^{BRT}$/CD146$^+$ marrow cells were typically larger and more granular than the nucleated erythroid cells and B-lymphocytes comprising the bulk of the STRO-1$^+$ population[29] (FIG. 1C-E). Cytospin preparations of STRO-1$^{BRT}$/CD146$^+$ sorted cells were found to be negative for the erythroid (glycophorin-A) and leukocyte (CD45) associated markers (data not shown). Confirmation that BMSSCs represented an early osteogenic precursor population was obtained by RT-PCR analysis of highly purified MACS/FACS-isolated STRO-1$^{BRT}$/CD146$^+$ cells, which failed to detect the early and late osteogenic, markers CBFA1 and osteocalcin, respectively (FIG. 1F). However, the progeny of STRO-1$^{BRT}$/CD146$^+$ sorted BMSSCs were found to express both CBFA1 and osteocalcin, following ex vivo expansion. Immunolocalization studies demonstrated that the CD146 antigen was predominantly expressed on blood vessel walls in sections of human bone marrow (FIG. 1G). Localization of both STRO-1 and CD146 was confined to large blood vessels in frozen sections of human bone marrow trephine (FIG. 1H).

Immunoselection protocols were subsequently used to determine if human DPSCs also expressed STRO-1 and CD146 in situ. The use of either MACS or FACS analysis to isolate DPSCs was restrictive due to the rarity of these cells (1 colony-forming cell per $2 \times 10^3$ cells plated) compounded by the limited number of pulp cells (approximately $10^5$ cells per pulp sample) obtained following processing. To circumvent this, we pooled several pulp tissues obtained from 3 to 4 different third molars per experiment and employed immunomagnetic bead selection on single cell suspensions of pulp tissue, based on their expression of either the STRO-1 or CD146 antigens. The STRO-1$^+$ fraction represented approximately 6% of the total pulp cell population. Comparative studies demonstrated that growth rates of individual colonies were unperturbed in the presence of magnetic beads (data not shown). Colony efficiency assays indicated that the majority of dental pulp derived colony-forming cells (82%) were represented in the minor, STRO-1$^+$ cell fraction analogous to BMSSCs (FIG. 2). The mean incidence of DPSCs in the STRO-1 positive fraction (329 colony-forming cells per $10^5$ cells plated±56 SE, n=3) was six-fold greater than unfractionated pulp cells (55 colony-forming cells per $10^5$ cells plated±14 SE, n=3). Using a similar strategy, different fractions of human dental pulp cells were selected based on their reactivity with the antibody, CC9. Colony efficiency assays showed that a high proportion (96%) of dental pulp-derived clonogenic colonies were also present in the CD146$^+$ population, using immunomagnetic Dynal bead selection (FIG. 2). The mean incidence of clonogenic colonies in the CD146$^+$ fraction (296 colony-forming cells per $10^5$ cells plated±37 SE, n=3) was seven-fold greater than unfractionated pulp cells (42 colony-forming cells per $10^5$ cells plated±9 SE, n=3).

Immunolocalization studies showed that STRO-1 expression was restricted to blood vessel walls and perineurium surrounding the nerve bundles, but was not present in the mature odontoblast layer or fibrous tissue, in frozen sections of human dental pulp tissue (FIG. 3A-B). Furthermore, co-localization of CD146 with STRO-1 was detected on the outer blood vessel cell walls, with no reactivity to the surrounding fibrous tissue, odontoblast layer, and the perineurium of the nerve (FIG. 3C-D). Importantly, expression of human odontoblast-specific differentiation marker, dentinsialoprotein (DSP), was restricted to the outer pulpal layer containing mature odontoblasts (FIG. 3E) and was absent in fibrous tissue, nerve bundles and blood vessels.

Differential Expression of the Perivascular Marker 3G5 by BMSSCs and DPSCs.

In the present study, flow cytometric analysis revealed that the cell surface antigen, 3G5, was highly expressed by a large proportion (54%) of hematopoietic marrow cells (FIG. 4A). This observation eliminated 3G5 as a candidate marker for isolating purified populations of BMSSCs directly from aspirates of human marrow. In addition, dual-FACS analysis based on 3G5 and STRO-1 expression was not possible since both antibodies shared the same isotype. Nevertheless, in vitro colony efficiency assays for different 3G5/CD146 FACS sorted subfractions demonstrated that only a minor proportion (14%) of bone marrow clonogenic colonies expressed the 3G5 antigen at low levels (FIG. 4B). Conversely, a larger proportion (63%) of clonogenic DPSCs (192 colony-forming cells per $10^5$ cells plated ±18.4 SE n=3) were present in the 3G5$^+$ cell fraction following immunomagnetic bead selection (FIG. 2). 3G5 demonstrated specific reactivity to pericytes in frozen sections of human dental pulp tissue (FIG. 3F).

We next analyzed the expression of more specific markers of endothelial cells (von Willebrand Factor) and smooth muscle cells/pericytes (α-smooth muscle actin) on cytospin preparations using freshly isolated STRO-1$^{BRT}$/CD146$^+$ BMSSCs and CD146$^+$ expressing DPSCs. A large proportion of purified BMSSCs (67%), were found to be positive for α-smooth muscle actin (FIG. 5A), but lacked expression of von Willebrand Factor (FIG. 5B). Similarly, the majority of isolated DPSCs (85%) were also found to express α-smooth muscle actin, but not von Willebrand Factor (FIG. 5C, 5D). Purified populations of STRO-1$^{BRT}$/CD146$^+$ BMSSCs and CD146$^+$ DPSCs were subsequently expanded in vitro then transplanted into immunocompromised mice to assess their developmental potentials in vivo. The progeny of cultured BMSSCs and DPSCs displayed distinct capacities, capable of regenerating the bone marrow and dental/pulp microenvironments, respectively (FIG. 5E, F), and appeared identical to the developmental potential of non-selected multi-colony derived BMSSCs and DPSCs (4).

Discussion

The present study provides direct evidence that two mesenchymal stem cell populations, distinct in their ontogeny and developmental potentials, are both associated with the microvasculature of their respective tissues.

We employed different Immunoselection protocols to demonstrate that BMSSCs and DPSCs could be efficiently retrieved from bone marrow aspirates and enzyme digested pulp tissue respectively, based primarily on their high expression of the STRO-1 antigen. This cell surface antigen is present on precursors of various stromal cell types including, marrow fibroblasts, osteoblasts, chondrocytes, adipocytes, and smooth muscle cells isolated from human adult and fetal bone marrow.[29,32-34] Previous studies have implicated STRO-1 as a marker of pre-osteogenic populations, where its expression is progressively lost following cell proliferation and differentiation into mature osteoblasts in vitro.[27,35,36] The STRO-1 antigen was also found to be present on the outer cell walls of human bone marrow and dental pulp blood vessels, in accord with previous studies that localized STRO-1 on large blood vessels, but not capillaries, in different adult tissues such as brain, gut, heart, kidney, liver, lung, lymphnode, muscle, thymus.[6] Therefore, STRO-1 appears to be an early marker of different mesenchymal stem cell populations and infers a possible perivascular niche for these stem cell populations in situ.

To determine if BMSSCs and DPSCs were associated directly with blood vessels we utilized another antibody (CC9),[28] which recognizes the immunoglobulin super family member, CD146 (MUC-18/Mel-CAM), known to be present on smooth muscle, endothelium, myofibroblasts and Schwann cells in situ, as well as being a marker for some human neoplasms.[37] Notably, CD146 is not expressed by bone marrow hematopoietic stem cells, nor their progenitors. While the precise function of CD146 is not known, it has been linked to various cellular processes including cell adhesion, cytoskeletal reorganization, cell shape, migration and proliferation through transmembrane signaling.

In order to dissect the BMSSC population, STRO-1$^{BRT}$ expressing marrow cells were further distinguished from STRO-1$^+$ hematopoietic cells (predominantly glycophorin-A$^+$ nucleated erythrocytes) based on their expression of CD146, using dual-FACS analysis. Purified STRO-1$^{BRT}$/CD146$^+$ human BMSSCs displayed light scatter properties characteristic of large granular cells. Our study supports the findings of Van Vlasselaer and colleagues (1994)[38] who isolated partially purified BMSSCs from murine bone marrow following 5-fluoracil (5-FU) treatment, and identified this population as having high perpendicular and forward light scatter characteristics. Interestingly, freshly isolated 5-FU resistant murine BMSSCs were also found to be positive for two perivascular markers Sab-1 and Sab-2.[38] Conversely, more recent studies have shown that when BMSSCs are cultivated in vitro, the most primitive populations display low perpendicular and forward light scatter properties[39] and therefore may not reflect the true morphology of BMSSC in situ. In the present study, STRO-1$^{BRT}$/CD146$^+$ sorted human BMSSCs lacked the expression of CBFA1 and osteocalcin that identify committed early and late osteogenic populations, respectively,[40,41] indicating that BMSSCs exhibit a pre-osteogenic phenotype in human bone marrow aspirates. We found that a high proportion of freshly isolated STRO-1$^{BRT}$/CD146$^+$ BMSSCs expressed α-smooth muscle actin, but not the endothelial specific marker von Willebrand Factor, providing direct evidence that this primitive precursor population displays a characteristic perivascular phenotype.

The present study also demonstrated the efficacy of using magnetic bead selection to isolate and enrich for DPSCs directly from human dental pulp tissue based on their expression of either STRO-1 or CD146. Immunolocalization of CD146 appeared to be specific to the microvasculature within dental pup. Co-localization of both STRO-1 and CD146 on the outer walls of large blood vessel in dental pulp tissue, implied that the majority of DPSCs arise from the microvasculature. However, since the STRO-1 antibody also reacted with the perineurium in dental pulp and peripheral nerve bundles (unpublished observations), further investigation is required to determine the role of this antigen in neural cell development.

Analogous to BMSSCs, freshly isolated CD146$^+$ DPSCs were found to express α-smooth muscle actin but not von Willebrand Factor. DPSCs were also shown to be an immature pre-odontogenic population both by their location distal from the dentin forming surface and by their lack of expression of the human odontoblast-specific dentin sialoprotein (DSP), which is restricted to the outer pulpal layer containing differentiated odontoblasts. We have previously described that ex vivo expanded human DPSCs do not express the precursor molecule, dentinsialophosphoprotein (DSPP), in vitro when cultured under non-inductive conditions.[4] Similar studies have shown that DSPP mRNA was highly expressed in freshly isolated odontoblast/pulp tissue, but was not detect in cultured dental papilla cells derived from rat incisors.[43,44] It is only when DPSCs are induced, either in vitro,[45] or by in vivo transplantation to form an ordered dentin matrix that DSPP is expressed.[4]

In vitro studies of ex viva expanded BMSSCs and DPSCs supported the notion that their progeny were morphologically similar to cultured perivascular cells having a bi-polar fibroblastic, stellar or flat morphology, rather than a polygonal endothelial-like appearance. In addition, we have previously shown that the progeny of BMSSC- and DPSC-derived colonies exhibit heterogeneous staining for both CD146 and α-smooth muscle actin, but lack expression of the endothelial markers, CD34 and von Willebrand Factor, in vitro.[4]

The observations that two different mesenchymal stem cell populations such as BMSSCs and DPSCs harbour in perivascular niches may have further implications for identifying stem cell populations in other adult tissues. Recent findings have identified human "reserve" multi-potent mesenchymal stem cells in connective tissues of skeletal muscle, and dermis derived from human fetal and adult samples.[56] However the exact location, developmental potential and ontogeny of these stem cells is still largely unknown. In the present study, identification of mesenchymal stem cell niches in bone marrow and dentin pulp may help elucidate the fundamental conditions necessary to selectively maintain and expand primitive multi-potential populations in vitro, in order to direct their developmental potentials in vivo.

EXAMPLE 2

Adult Human Bone Marrow MPC are Distinct from Stromal Precursor Cells, Haematopoietic Stem Cells and Angioblasts by their High Expression of the STRO-1 Antigen and Lack of CD34 Expression Postnatal bone marrow appears to be a hub of residential stem and precursor cell types responsible for blood cell formation (haematopoietic stem cells), endothelial development (angioblast), and connective tissue/stromal differentiation (stromal precursor cells/bone marrow stromal stem cells/mesenchymal stem cells). Recent work by our group (Gronthos et al. 2003; Shi and Gronthos 2003) has, for the first time, purified and characterised human multipotential bone marrow mesenchymal precursor cells (MPC) based on their high expression of the STRO-1 antigen and by their co-expression of the immunoglobulin superfamily members, VCAM-1 (CD106) and MUC-18 (CD146). Early studies by Simmons and Torok-Storb (1991a and b), have shown that bone marrow-derived STRO-1$^+$ stromal precursor cells, with the capacity to form adherent colonies in vitro, also expressed the haematopoietic stem cell marker, CD34, albeit at low levels. These studies used CD34 antibody-complement mediated cell lysis to eliminate a high proportion of adherent colony-forming cells in marrow aspirates (Simmons and Torok-Storb 1991b). It is important to note that while the STRO-1 antibody was generated following immunisation of mice with human CD34$^+$ bone marrow cells, this may have arisen due to the fact that the STRO-1 antigen is also expressed at moderate to low levels on CD34$^+$/Glycophorin-A$^+$ nucleated red cells and CD34$^+$/CD20$^+$ B-lymphocytes. We now offer direct evidence, using sophisticated fluorescence activated cell sorting technology that multipotential adult human bone marrow MPC express high levels of STRO-1, but lack expression to the stromal precursor cell, haematopoietic stem cell and angioblast maker (CD34), the leukocyte antigen (CD45), and the nucleated red cell marker (Glycophorin-A) (FIG. 6A-C). These data demonstrate that adult human bone marrow-derived MPC are a novel stem cell population, distinct from more mature stromal precursor cells, haematopoietic stem cells and angioblast (FIG. 7).

Unless otherwise indicated the materials and methods of this example are the same as those for Example 1.

FIG. 6. Expression of CD34, CD45 and Glycophorin-A on STRO-1 positive bone marrow mononuclear cells. Representative histograms depicting typical dual-colour flow cytometric analysis profiles of STRO-1 positive bone marrow mononuclear cells isolated initially by magnetic activated sorting and co-stained with antibodies directed against CD34 (A), CD45 (B) or Glycophorin-A (C). The STRO-1 antibody was identified using a goat anti-murine IgM-fluorescein isothiocyanate while CD34, CD45 and Glycophorin-A were identified using a goat anti-murine IgG-phycoerythrin. The high expressing STRO-1 fraction which contained the clonogenic MPC population was isolated by fluorescence activated cell sorting based on regions R1 and R2.

FIG. 7. Bone marrow MPC are STRO-1 bright, CD34 negative, CD45 negative and Glycophorin-A negative. The graph depicts the results of in vitro adherent colony formation assays performed for each of the different sorted STRO-1 bright populations selected by their co-expression or lack of either the CD34, CD45 or Gycophorin-A antigens, based on regions R1 and R2 as indicated in FIG. 6. These data are expressed as the mean incidence of colony-forming units for each cell fraction averaged from two separate experiments.

EXAMPLE 3

Identification of Multipotential MPC in Different Human Tissues

While the existence and precise location of MPC in different tissues is largely unknown, we have recently demonstrated that MPC appear to reside in a perivascular niche in human bone marrow and dental pulp tissues (Shi and Gronthos 2003). These observations were based on a combination of immunohistochemical and immunoselection methods to identify and isolate different MPC populations based on their expression of the mesenchymal stem cell marker, STRO-1, the smooth muscle and pericyte markers, CD146, alpha-smooth muscle actin and the pericyte specific marker, 3G5. We have now extended these studies demonstrating the co-localization of STRO-1/CD146, STRO-1/alpha-smooth muscle actin, and 3G5/CD146 antigens in a wider variety of tissues including heart, liver, kidney, skin, spleen, pancreas, lymph node (FIG. 8).

To confirm our earlier findings that MPC can be derived from non-bone marrow tissue such as dental pulp, we used fluorescence activated cell sorting to isolate different MPC populations from adult human peripheral adipose. Single cell suspensions were obtained following digestion of the adipose tissue with collagenase and dispase as previously described (Shi and Gronthos 2003). The adipose-derived cells were then incubated with antibodies reactive against STRO-1, CD146 and 3G5. Cell populations were then selected by FACS, based on their positivity (region R3) or negativity (region R2) to each marker and then plated into regular growth medium (Shi and Gronthos 2003) to assess the incidence of adherent colony-forming cells in each cell fraction (FIG. 9). Following 12 days of culture, colonies (aggregates of 50 cells or more) were scored and displayed as the number of colonies per $10^5$ cells plated for each cell fraction. Our data demonstrated that MPC can be derived from adipose tissues based on their expression of STRO-1/3G5/CD146 antigens (FIG. 10). Dual colour flow cytometric analysis confirmed that only a minor proportion of adipose-derived cells co-expressed STRO-1/CD146 and 3G5/CD146 (FIG. 11). These findings are consistent with our previous observations that MPC can be isolated from both bone marrow and dental pulp tissue based on the same set of perivascular markers (Shi and Gronthos 2003). Furthermore, we provide evidence demonstrating that adipose derived MPC isolated by CD146 selection have the capacity to differentiate into different tissues such as bone, fat and cartilage (FIG. 12), as previous described (Gronthos et al. 2003).

Recent findings examining the existence of MPC in unrelated tissues such as skin has also been examined to further strengthen our hypothesis. Single cell suspensions were obtained following digestion of full thickness human skin with collagenase and dispase as described above for human adipose tissue. The skin-derived cells were then incubated with antibodies reactive against STRO-1, CD146 and 3G5 identified using either a goat anti-murine IgM or IgG-phycoerythrin. Cell populations were then selected by FACS, based on their positivity (region R3) or negativity (region R2) to each marker and then plated into regular growth medium (Shi and Gronthos 2003) to assess the incidence of adherent colony-forming cells in each cell fraction (FIG. 13). Following 12 days of culture, colonies (aggregates of 50 cells or more) were scored and displayed as the number of colonies per $10^5$ cells plated for each cell fraction. The data demonstrated that MPC can also be derived from skin based on their expression of STRO-1/3G5/CD146 antigens (FIG. 10). Collectively these data suggest that multipotential MPC can be identified and isolated in virtually all vascularised tissues derived from postnatal human tissue based on a common phenotype.

Unless otherwise indicated the materials and methods of this example are the same as those for Example 1.

FIG. 8. Reactivity of perivascular makers in different human tissues. Dual-colour immunofluorescence staining demonstrating reactivity of (A) STRO-1 and CD146, (B) STRO-1 and alpha-smooth muscle actin, and (C) 3G5 and CD146, on blood vessels and connective tissue present on spleen, pancreas (FIG. 8A), brain, kidney (FIG. 8B), liver, heart (FIG. 8C) and skin (FIG. 8D) 20×. The STRO-1 and 3G5 antibodies were identified using a goat anti-murine IgM-Texas Red while CD146 and alpha-smooth muscle actin were identified using a goat anti-murine or IgG-fluorescein isothiocyanate. Co-localization is indicated by overlaping areas of yellow and orange fluorescence (white arrows).

FIG. 9. Isolation of adipose-derived MPC by FACS. Representative flow cytometric histograms depicting the expression of STRO-1 (A), CD146 (B) and 3G5 (C) in fresh preparations of peripheral adipose-derived single-cell suspensions generated following collagenase/dispase digestion as previously described (Shi and Gronthos 2003). The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

FIG. 10. Clonogenic adipose-derived MPC are positive for STRO-1/3G5/CD146. The bar graph depicts the number of clonogenic colonies retrieved from single cell suspensions of enzymatically digested human peripheral adipose tissue, following fluorescence activated cell sorting, based on their reactivity to antibodies that recognize STRO-1, CD146, and 3G5 (FIG. 9), then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

FIG. 11. Immunophenotypic analysis of adipose-derived MPC. Representative flow cytometric histograms depicting the co-expression of STRO-1 and CD146 (A) and 3G5 and CD146 (B) in fresh preparations of peripheral adipose-derived single-cell suspensions generated following collagenase/dispase digestion. The STRO-1 and 3G5 antibodies were identified using a goat anti-murine IgM-phycoerythrin while CD146 was identified using a goat anti-murine IgG-fluorescein isothiocyanate. Approximately 60% and 50% of the CD146 positive cells co-express STRO-1 and 3G5, respectively. These data suggest that 10% or more of the CD164 positive cells co-express STRO-1 and 3G5.

FIG. 12. Developmental potential of purified Adipocyte-derived MPC in vitro. Preparations of primary MPC cultures derived from STRO-1+/CD146+ adipose cells were re-cultured either in standard culture conditions (A), osteogenic inductive medium (B), Adipogenic inductive medium (C) or condrogenic conditions (D) as previously described Gronthos et al. 2003. Following two weeks of multi-differentiation induction, the adipocyte-derived MPC demonstrated the capacity to form bone (B; Alizarin positive mineral deposits), fat (C; Oil Red O positive lipid) and cartilage (D: collagen type II matrix).

FIG. 13. Isolation of skin-derived MPC by FACS. Representative flow cytometirc histograms depicting the expression of STRO-1, CD146 and 3G5 in fresh preparations of full thickness skin-derived single-cell suspensions generated following collagenase/dispase digestion. The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

FIG. 14. Clonogenic skin-derived MPC are positive for STRO-1bri/3G5/CD146. The bar graph depicts the number of adherent colonies recovered from single cell suspensions of enzymatically digested human skin, following fluorescence activated cell sorting, based on their reactivity to antibodies that recognize STRO-1, CD146, and 3G5, then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

EXAMPLE 4

Immunophenotypic Analysis of ex vivo Expanded Human Bone Marrow Mesenchymal Precursor Cells We have previously reported that multipotential mesenchymal precursor cells (MPC) can be purified from adult human bone marrow mononuclear cells based on the phenotype STRO-1$^{bright}$/VCAM-1 (CD106)+ or STRO-1$^{bright}$/MUC-18 (CD146)+ (Gronthos et al. 2003; Shi and Gronthos 2003). The MPC population can be readily propagated in vitro under defined culture conditions (Gronthos et al. 2003). We now present data characterising the ex vivo expanded MPC progeny based on markers associated with different cell lineages, at both the mRNA and protein level, using reverse transcriptase-polymerase chain reaction (RT-PCR) and flow cytometric analysis, respectively.

In the first series of experiments, semi-quantitative RT-PCR analysis was employed to examine the gene expression profile of various lineage-associated genes present in the cultured MPC populations (FIG. 15). Relative gene expression for each cell marker was assessed with reference to the expression of the house-keeping gene, GAPDH, using ImageQuant software (FIG. 15 B). In addition, single-colour flow cytometric analysis was used to examine the protein expression profile of ex vivo expanded MPC based on their expression of cell lineage-associated markers (FIG. 15 A). A summary of the general phenotype based on the gene and protein expression of the cultured MPC is presented in Table 1. Direct comparison of the gene expression profile of MPC described in the present patent demonstrated clear differences between this cell population and mesenchymal stem cells (MSC) previously described by Pittenger et al. 1999, (Table 1).

Unless otherwise indicated the materials and methods of this example are the same as those for Example 1.

FIG. 15 A. Immunophenotypic expression pattern of ex vivo expanded bone marrow MPC. Single cell suspensions of ex vivo expanded bone marrow MPC were prepared by trypsin/EDTA treatment then incubated with antibodies identifying cell lineage-associated markers. For those antibodies identifying intracellular antigens, cell preparations were fixed with cold 70% ethanol to permeanbilize the cellular membrane prior to staining for intracellular markers. Isotype snatched control antibodies were treated under identical conditions. Flow cytometric analysis was performed using a COULTER EPICS instrument. The dot plots represent 5,000 listmode events indicating the level of fluorescence intensity for each lineage cell marker (bold line) with reference to the isotype matched negative control antibodies (thin line).

FIG. 15 B. Gene expression profile of cultured MPC. Single cell suspensions of ex vivo expanded bone marrow MPC were prepared by trypsin/EDTA treatment and total cellular RNA was prepared. Using RNAzolB extraction method total RNA was isolated and used as a template for cDNA synthesis, prepared using standard procedure. The expression of various transcripts was assessed by PCR amplification, using a standard protocol as described previously (Gronthos et al. 2003). Primers sets used in this study are shown in Table 2. Following amplification, each reaction mixture was analysed by 1.5% agarose gel electrophoresis, and visualised by ethidium bromide staining. Relative gene expression for each cell marker was assessed with reference to the expression of the house-keeping gene, GAPDH, using ImageQuant software.

FIG. 16. Ex vivo expanded STRO-1$^{bri}$ MPC can develop into arterioles in vitro. Single cell suspensions of ex viva expanded bone marrow STRO-1$^{bri}$ and STRO-1$^{dull}$ MPC were prepared by trypsin/EDTA treatment then plated into 48-well plates containing 200 µl of matrigel. The STRO-1$^{dull}$ (A) and STRO-1$^{bri}$ (B) MPC were plated at 20,000 cells per well in serum-free medium (Gronthos et al. 2003) supplemented with the growth factors PDGF, EGF, VEGF at 10 ng/ml. Following 24 hours of culture at 37° C. in 5% $CO_2$, the wells were washed then fixed with 4% paraformaldehyde. Immunohistochemical studies were subsequently performed demonstrated that the cord-like structures expressed alpha-smooth muscle actin identified with a goat-anti-murine IgG horse radish peroxidase antibody.

TABLE 1

Comparison between cultured human Mesenchymal Precursor Cells (MCP's) and cultured human Mesenchymal Stem Cells (MSC's) following ex vivo expansion. Antigens found to be present on cell surface, intracellular or in the extra cellular matrix. MPCs express markers of tissues with different developmental origin, ie. ECT-ectoderm, MES-mesoderm and END-endoderm.

| ANTIGEN | MSC | MPC | Differentiated Cell Type. |
|---|---|---|---|
| STRO-1 | −ve | +ve | |
| Collagen II | −ve | +ve | Chondrocyte (MES) |
| Collagen IV | −ve | +ve | Fibroblast (MES) |
| Laminin | −ve | +ve | Fibroblast (MES) |
| Bone Sialoprotein (BSP) | −ve | +ve | Osteoblast (MES) |
| Osteocalcin (OCN) | −ve | +ve | Osteoblast (MES) |
| Nestin | ND | +ve | Neural (ECT) |
| Glial Fibrillary Acidic Protein (GFAP) | ND | +ve | Neural (ECT) |
| CBFA1 | −ve | +ve | Osteoblast (MES) |
| Osterix (OSX) | ND | +ve | Osteoblast (MES) |
| Osteocalcin (OCN) | −ve | +ve | Osteoblast (MES) |
| Sox9 | ND | +ve | Chondrocyte (MES) |
| Collagen X (COL X) | +ve | +ve | Chondrocyte (MES) |
| Leptin | ND | +ve | Adipose (MES) |
| GATA-4 | ND | +ve | Cardiomyocyte (MES) |
| Transferrin (TFN) | ND | +ve | Hepatocyte (END) |
| Flavin Containing Monooxygenase (FCM) | ND | +ve | Hepatocyte (END) |

TABLE 2

RT-PCR primers and conditions for the specific amplification of human mRNA

| Target Gene | Sense/Antisense (5-3) Primer Sequences | Product Size |
|---|---|---|
| GAPDH | CACTGACACGTTGGCAGTGG/ [SEQ ID NO. 7] CATGAGAAGGCTGGGGCTC [SEQ ID NO. 8] | 417 |
| Leptin | ATGCATTGGGAACCCTGTGC/ [SEQ ID NO. 9] GCACCCAGGGCTGAGGTCCA [SEQ ID NO. 10] | 492 |
| CBFA-1 | GTGGACGAGGCAAGAGTTTCA/ [SEQ ID NO. 11] TGGCAGGTAGGTGTGGTAGTG [SEQ ID NO. 12] | 632 |
| OCN | ATGAGAGCCCTCACACTCCTC/ [SEQ ID NO. 13] CGTAGAAGCGCCGATAGGC [SEQ ID NO. 14] | 289 |
| GFAP | CTGTTGCCAGAGATGGAGGTT/ [SEQ ID NO. 15] TCATCGCTCAGGAGGTCCTT [SEQ ID NO. 16] | 370 |
| Nestin | GGCAGCGTTGGAACAGAGGTTGGA/ [SEQ ID NO. 17] CTCTAAACTGGAGTGGTCAGGGCT [SEQ ID NO. 18] | 460 |
| GATA-4 | GACTTCTCAGAAGGCAGAG/ [SEQ ID NO. 19] CTATCCTCCAAGTCCCAGAG [SEQ ID NO. 20] | 800 |
| PDGFβ-R | AATGTCTCCAGCACCTTCGTT [SEQ ID NO. 21] AGCGGATGTGGTAAGGCATA [SEQ ID NO. 22] | 650 |
| Osterix | GGCACAAAGAAGCCGTACTC/ [SEQ ID NO. 23] CACTGGGCAGACAGTCAGAA [SEQ ID NO. 24] | 247 |
| COL X | AGCCAGGGTTGCCAGGACCA/ [SEQ ID NO. 25] TTTTCCCACTCCAGGAGGGC [SEQ ID NO. 26] | 387 |
| SOX9 | CTC TGC CTG TTT GGA CTT TGT/ [SEQ ID NO. 27] CCT TTG CTT GCC TTT TAC CTC [SEQ ID NO. 28] | 598 |
| Ang-1 | CCAGTCAGAGGCAGTACATGCTAAGAATTGAGTTA/ [SEQ ID NO. 29] GTTTTCCATGGTTTTGTCCCGCAGTA [SEQ ID NO. 30] | 300 |

REFERENCES

1. Spradling et al., (2001). *Nature* 414(6859):98-104.
2. Bianco and Robey (2001) *Nature* 414(6859):118-121.
3. Fuchs and Segre (2000) *Cell* 100(1):143-55.
4. Gronthos et al., (2000) *Proc Natl Acad Sci USA* 97(25): 13625-30.
5. Kuznetsov et al., (1997). *J Bone Miner Res* 12(9):1335-47.
6. Bianco et al., (2001) *Stem Cells* 19(3):180-92.
7. Lichtman (1981) *Exp Hematol* 9(4):391-410.
8. Weiss (1976) *Anatomical Record* 186:161-84.
9. Weiss and Sakai H (1984) *Am J Anat* 170(3):447-63.
10. Dexter and Shadduck (1980) *J Cell Physiol* 102(3):279-86.
11. Orchardson amd Cadden (2001) *Dent Update* 28(4):200-6, 208-9.
12. Peters and Balling (1999) *Trends Genet* 15(2):59-65.
13. Thesleff and Aberg (1999) *Bone* 25(1):123-5.
14. Friedenstein et al., (1974) *Transplantation* 17(4):331-40.
15. Castro-Malaspina et al., (1980) *Blood* 56(2):289-301.
16. Weissman (2000) *Cell* 100(1):157-68.
17. Uchida et al., (2000) *Proc Natl Acad Sci USA* 97(26): 14720-5.
18. Kuznetsov et al., (2001) *J Cell Biol* 153(5):1133-40.
19. Shi et al. (2001) *Bone* 29(6):532-39.
20. Pittenger et al., (1999) *Science* 284(5411):143-7.
21. Gronthos et al., (2002) *J Dent Res* 81(8):531-5.
22. Owen and Friedenstein (1988) *Ciba Found Symp* 136 (29):42-60.
23. Doherty et al., (1998) *J Bone Miner Res* 13(5):828-38.
24. Bianco and Cossu (1999). *Exp Cell Res* 251(2):257-63.
25. Gronthos et al., (1998) Isolation, purification and in vitro manipulation of human bone marrow stromal precursor cells. In: Beresford J N and Owen M E (ed) Marrow stromal cell culture. Cambridge University Press, Cambridge, UK, pp 26-42.
26. Gronthos and Simmons (1995) *Blood* 85(4):929-40.
27. Gronthos et al., (1999) *J Bone Miner Res* 14(1):47-56.

28. Filshie et al., (1998) *Leukemia* 12(3):414-21.
29. Simmons and Torok-Storb (1991). *Blood* 78(1):55-62.
30. Canfield and Schor (1998) Osteogenic potential of vascular pericytes. In: Beresford J N and Owen M E (ed) Marrow stromal cell culture. Cambridge University Press, Cambridge, UK, pp 128-148.
31. Riminucci and Bianco (1998) The bone marrow stroma in vivo: ontogeny, structure, cellular composition and changes in disease. In: Beresford J N and Owen M E (ed) Marrow stromal cell culture. Cambridge University Press, UK, Cambridge, UK, pp 10-25.
32. Gronthos et al., (1994) *Blood* 84(12):4164-73.
33. Oyajobi et al., (1999) *J Bone Miner Res* 14(3):351-61.
34. Dennis et al., (2002). *Cells Tissues Organs* 170(2-3):73-82.
35. Stewart et al., (1999) *J Bone Miner Res* 14(8):1345-56.
36. Alidjoudj et al., (2001) *J Cell Biochem* 81(1):23-38.
37. Shih (1999) *J Pathol* 189(1):4-11.
38. Van Vlasselaer et al., (1994) *Blood* 84(3):753-63.
39. Prockop et al., (2001). Cytotherapy 3(5):393-6.
40. Ducy et al., (1997) *Cell* 89(5):747-54.
41. Komori et al., (1997) *Cell* 89(5):755-64.
42. Woodbury et al., (2000) *J Neurosci Res* 61(4)364-70.
43. Dey et al., (2001) *Arch Oral Biol* 46(3):249-60.
44. Ueno et al., (2001) *Matrix Biol* 20(5-6):347-55.
45. Couble et al., (2000) *Calcif Tissue Int* 66(2):129-38.
46. Nehls and Drenckhahn (1993) *Histochemistry* 99(1):1-12.
47. Schor et al., (1995) *Clin Orthop* 313:81-91.
48. Pugach et al., (1999) *Arkh Patol* 61(4):18-21.
49. Nehls et al., (1992) *Cell Tissue Res* 270(3):469-74.
50. Brighton et al., (1992) *Clin Orthop* 275:287-99.
51. Nayak et al., (1988) *J Exp Med* 167(3):1003-15.
52. Andreeva et al., (1998) *Tissue Cell* 30(1):127-35.
53. Cattoretti et al., (1993) *Blood* 81(7):1726-38.
54. Charbord et al., (2000) *J Hematother Stem Cell Res* 9(6):935-43.
55. Dennis and Charbord (2002) *Stem Cells* 20(3):205-14.
56. Young et al., (2001) *Anat Rec* 263(4):350-60.
Gronthos et al., (2003). *Journal of Cell Science* 116: 1827-1835.
Pittenger et al., (1999). *Science* 284, 143-7.
Simmons and Torok-Storb (1991a). *Blood* 78(1):55-62.
Simmons and Torok-Storb (1991 b). *Blood* 78:2848.
Shi and Gronthos. (2003). *Journal of Bone and Mineral Research*, 18(4): 696-704.

The invention claimed is:

1. A therapeutic composition comprising a suspension of culture expanded mammalian mesenchymal precursor cells (MPCs), wherein the culture expanded cells are derived from adipose tissue cells that are multipotent and at least 1% of the culture expanded cells are positive for the surface marker 3G5 and one or both of the surface markers MUC18/CD146 and STRO-1.

2. The therapeutic composition of claim 1, wherein the MPCs co-express the marker alpha-smooth muscle actin.

3. The therapeutic composition of claim 1, wherein the MPCs co-express the marker STRO-1$^{bri}$.

4. The therapeutic composition of claim 1, wherein the MPCs co-express a marker selected from, but not limited to, the group comprising THY-1, VCAM-1, ICAM-1, PECAM-1, CD49a/CD49b/CD29, CD49c/CD29, CD49d/CD29, CD29, CD61, integrin beta 5, 6-19, thrombomodulin, CD10, CD13, SCF, STRO-1$^{bri}$, PDGF-R, EGF-R, IGF1-R, NGF-R, FGF-R, Leptin-R(Stro-2).

5. The therapeutic composition of claim 1, wherein the MPCs co-express the markers STRO-1$^{bri}$, MUC18/CD146, and alpha-smooth muscle actin.

6. The therapeutic composition of claim 1, wherein the MPCs are negative for the hematopoietic markers CD45, CD34, and glycophorin A.

7. The therapeutic composition of claim 1, wherein the MPCs are capable of forming a clonogenic colony and differentiating to three or more mesenchymal tissue types, isolated from a tissue of the group comprising, but not limited to, adipose tissue, teeth, dental pulp, skin, liver, kidney, heart, retina, brain, hair follicles, intestine, lung, spleen, lymph node, thymus, pancreas, bone, ligament, bone marrow, tendon, and skeletal muscle, and which are positive for the surface marker STRO-1$^{bri}$.

8. The therapeutic composition of claim 7 wherein the MPCs co-express the marker MUC-18/CD146 or alpha-smooth muscle actin.

9. The therapeutic composition of claim 7 wherein the MPCs co-express a marker selected from, but not limited to, the group comprising THY-1, VCAM-1, ICAM-1, PECAM-1, CD49a/CD49b/CD29, CD49c/CD29, CD49d/CD29, CD29, CD61, integrin beta 5, 6-19, thrombomodulin, CD10, CD13, SCF, STRO-1$^{bri}$, PDGF-R, EGF-R, IGF1-R, NGF-R, FGF-R, Leptin-R (STRO-2).

10. The therapeutic composition of claim wherein the MPCs are negative for the hematopoietic markers CD45, CD34, and glycophorin A.

11. The therapeutic composition of claim 1, wherein the mammal is a human.

12. The therapeutic composition of claim 1 wherein the MPCs have the capacity to be induced to differentiate to form cells comprising one or more of at least osteoblast, odontoblast, dentin-producing, chondrocyte, tendon, ligament, cartilage, adipocyte, fibroblast, marrow stroma, osteoclast- and hematopoietic-supportive stroma, cardiac muscle, smooth muscle, skeletal muscle, pericyte, vascular, epithelial, glial, neuronal, astrocyte or oligodendrocyte cell type.

13. The therapeutic composition of claim 1, wherein the composition is enriched for MPCs capable of forming a clonogenic colony and differentiating to three or more mesenchymal tissue types.

14. in the therapeutic composition of claim 13, wherein the MPCs are additionally positive for the marker STRO-1$^{bri}$.

15. in the therapeutic composition of claim 13, wherein the MPCs co-express MUC18/CD146, alpha-smooth muscle actin, STRO-1$^{bri}$, and 3G5.

16. The therapeutic composition of claim 13, wherein the MPCs are negative for the hematopoietic markers CD34, CD45, and glycophorin-A.

17. The therapeutic composition of claim 13, comprising at least 0.01% MPCs capable of forming a clonogenic colony and differentiating to three or more mesenchymal tissue types.

18. The therapeutic composition of claim 13, comprising at least 0.1% MPCs capable of forming a clonogenic colony and differentiating to three or more mesenchymal tissue types.

19. The therapeutic composition of claim 13, comprising at least 1% MPCs capable of forming a clonogenic colony and differentiating to three or more mesenchymal tissue types.

20. The therapeutic composition of claim 13, comprising at least 0.01% STRO-1$^{bri}$ MPCs.

21. The therapeutic composition of claim 13, comprising at least 0.1% STRO-1$^{bri}$ MPCs.

22. The therapeutic composition of claim 13, comprising at least 1% STRO-1$^{bri}$ MPCs.

23. The therapeutic composition of claim 13, wherein the MPCs have the capacity to be induced to differentiate to form cells comprising one or more of at least osteoblast, odontoblast, dentin-producing, chondrocyte, tendon, ligament, cartilage, adipocyte, fibroblast, marrow stroma, osteoclast- and hematopoietic-supportive stroma, cardiac muscle, smooth muscle, skeletal muscle, pericyte, vascular, epithelial, glial, neuronal, astrocyte, or oligodendrocyte cell type.

24. The therapeutic composition of claim 13, which comprises at least 0.1% cells which express at high levels one or more of the markers STRO-1, 3G5, or MUC18/CD146.

25. The therapeutic composition of claim 13, which comprises at least 1% cells which express at high levels one or more of the markers STRO-1$^{bri}$, 3G5, or MUC18/CD146.

26. The therapeutic composition of claim 13, which comprises at least 2% MPCs which express at high levels one or more of the markers STRO-1$^{bri}$, 3G5, or MUC18/CD146.

27. The therapeutic composition of claim 13, which comprises at least 5% cells which express at high levels one or more of the markers STRO-1$^{bri}$, 3G5, or MUC18/CD146.

28. The therapeutic composition of claim 13, which comprises at least 10% cells which express at high levels one or more of the markers STRO-1$^{bri}$, 3G5, or MUC18/CD146.

29. The therapeutic composition of claim 1, wherein at least 5% of the culture expanded cells are positive for the surface marker 3G5.

30. The therapeutic composition of claim 29, wherein the culture expanded cells that are positive for the surface marker 3G5 are also positive for the surface marker STRO-1.

* * * * *

```
                         SEQUENCE LISTING

<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
ctatggagag gacgccacgc ctgg                                           24

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
catagccatc gtagccttgt cct                                            23

<210> SEQ ID NO 3
<211> LENGTH: 16
<212> TYPE: DNA
<213> ORGANISM: Artificial Sequence
<220> FEATURE:
<223> OTHER INFORMATION: Primer

<400> SEQUENCE: 3
catgagagcc ctcaca                                                    16

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
agagcgacac cctagac                                                   17
```

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
agccgcatct tcttttgcgt c                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tcatatttgg caggtttttc t                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cactgacacg ttggcagtgg                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
catggagaag gctggggctc                                                20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
atgcattggg aaccctgtgc                                                20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcacccaggg ctgaggtcca                                                20

<210> SEQ ID NO 11
<211> LENGTH: 21
<212> TYPE: DNA
<213> ORGANISM: Artificial Sequence
<220> FEATURE:

<223> OTHER INFORMATION: Primer

<400> SEQUENCE: 11
gtggacgagg caagagtttc a                                              21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tggcaggtag gtgtggtagt g                                              21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
atgagagccc tcacactcct c                                              21

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
cgtagaagcg ccgataggc                                                 19

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
ctgttgccag agatggaggt t                                              21

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcatcgctca ggaggtcctt                                                20

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ggcagcgttg gaacagaggt tgga                                           24

```
<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ctctaaactg gagtggtcag ggct                                          24

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
gacttctcag aaggcagag                                                19

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ctatcctcca agtcccagag                                               20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
aatgtctcca gcaccttcgt                                               20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
agcggatgtg gtaaggcata                                               20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ggcacaaaga agccgtactc                                               20

<210> SEQ ID NO 24
<211> LENGTH: 20
<212> TYPE: DNA
<213> ORGANISM: Artificial Sequence
<220> FEATURE:
<223> OTHER INFORMATION: Primer
```

<400> SEQUENCE: 24
cactgggcag acagtcagaa                                            20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
agccagggtt gccaggacca                                            20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tttccccact ccaggagggc                                            20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ctctgcctgt ttggactttg t                                          21

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
cctttgcttg cctttttacct c                                         21

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
ccagtcagag gcagtacatg ctaagaattg agtta                           35

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
gttttccatg gttttgtccc gcagta                                     26